(12) United States Patent
Lu et al.

(10) Patent No.: US 7,807,180 B2
(45) Date of Patent: Oct. 5, 2010

(54) POXVIRUS METHODS AND COMPOSITIONS

(75) Inventors: Shan Lu, Hopkinton, MA (US); Pavlo Sakhatskyy, Worcester, MA (US); Shixia Wang, Northborough, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 11/842,761

(22) Filed: Aug. 21, 2007

(65) Prior Publication Data

US 2009/0053256 A1 Feb. 26, 2009

(51) Int. Cl.
*A61K 39/275* (2006.01)
*A61K 39/385* (2006.01)
*A61K 39/12* (2006.01)
*A61K 39/38* (2006.01)
*A61K 39/295* (2006.01)
*C12Q 1/37* (2006.01)
*C07H 21/02* (2006.01)
*A61K 39/17* (2006.01)

(52) U.S. Cl. ............. 424/232.1; 424/194.1; 424/204.1; 424/184.1; 424/202.1; 536/23.1; 435/6

(58) Field of Classification Search ........................ None
See application file for complete search history.

(56) References Cited

U.S. PATENT DOCUMENTS

| | | | |
|---|---|---|---|
| 5,670,367 | A | 9/1997 | Dorner et al. |
| 7,132,234 | B2 | 11/2006 | Lu et al. |
| 7,217,526 | B2 | 5/2007 | Terajima et al. |
| 2002/0176871 | A1 | 11/2002 | Hooper et al. |
| 2005/0031643 | A1 | 2/2005 | Szalay et al. |
| 2006/0003316 | A1 * | 1/2006 | Simard et al. ................. 435/5 |

FOREIGN PATENT DOCUMENTS

| | | |
|---|---|---|
| WO | 2003046138 | 6/2003 |
| WO | 2005/021707 | 3/2005 |
| WO | 2006076003 | 7/2006 |

OTHER PUBLICATIONS

Barrett et al., Optimization of codon usage of poxvirus genes allows for improved transient expression in mammalian cells, 2006, Virus Genes, vol. 33, pp. 15-26.*
Nelson and Cox, Principles of Biochemistry, $4^{th}$ Ed., 2005, Lehninger: W.H. Freeman and Company.*
Patterson et al., Codon optimization of bacterial luciferase (lux) for expressio in mammalian cells, 2005, Journal of Industrial Micbiology and Biotechnology, vol. 32, pp. 115-123.*
Mount and Conrad, Microcomputer programs for back translation of protein to DNA sequences and analysis of ambiguous DNA sequences, 1984, Nucleic Acids Research, vol. 12, No. 1, pp. 819-823.*
Sakhatskyy et al., Immunogenicity and protection efficacy of subunit-based smallpox vaccines using variola major antigens, 2008, Virology, vol. 371, pp. 98-107.*
Mercer and Traktman, "Genetic and Cell Biological Characterization of the Vaccinia Virus A30 and G7 Phosphoproteins," Journal of Virology, 79(11):7146-7161 (2005).
Sakhatskyy et al., "Immunogenicity and protection efficacy of monovalent and polyvalent poxvirus vaccines that include the D8 antigen," Virology, 355:164-174 (2006).

* cited by examiner

*Primary Examiner*—Zachariah Lucas
*Assistant Examiner*—Benjamin P Blumel
(74) *Attorney, Agent, or Firm*—Fish & Richardson P.C.

(57) ABSTRACT

Methods and compositions for inducing immune responses against poxviruses are disclosed. The compositions include nucleic acids that encode modified vaccinia and variola antigens. Compositions that include recombinant vaccinia and variola polypeptides are also disclosed.

9 Claims, 9 Drawing Sheets

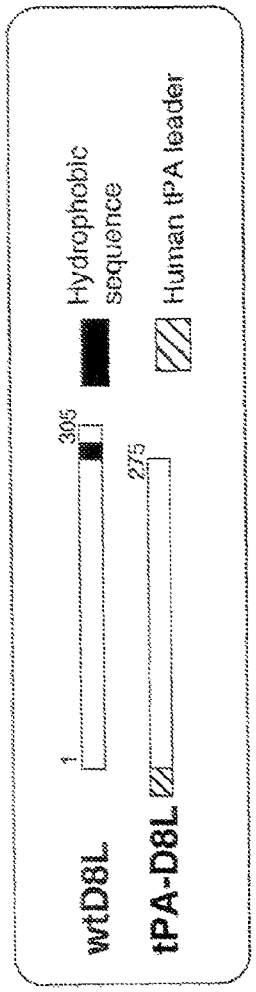
FIG. 1
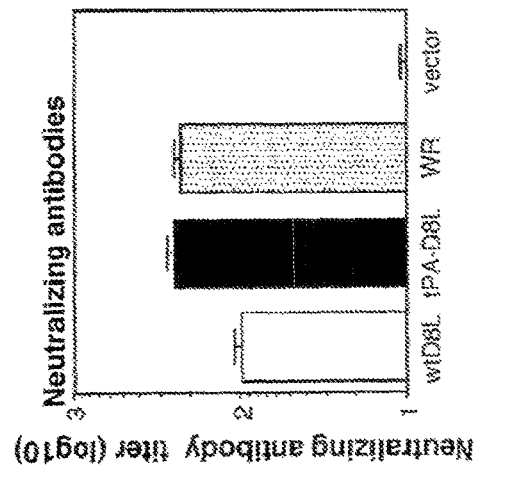
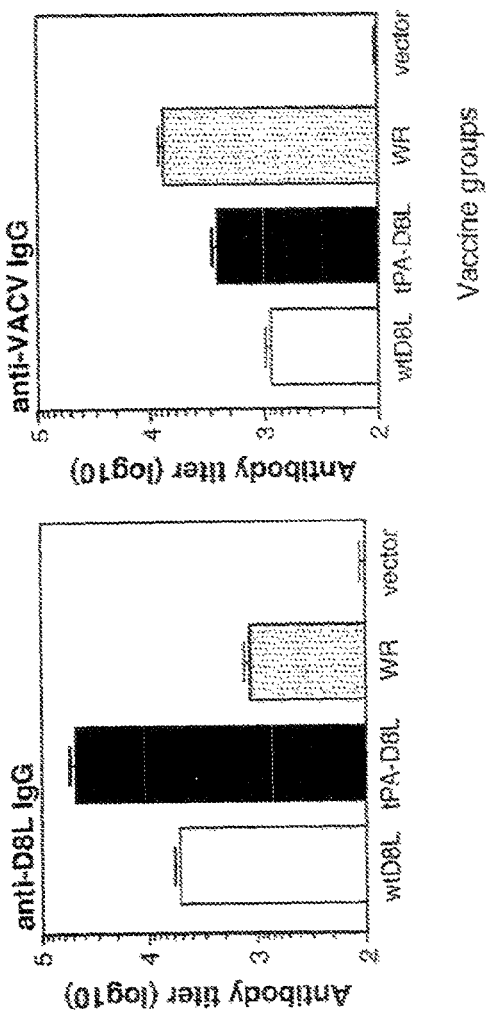
FIG. 2A  FIG. 2B  FIG. 2C

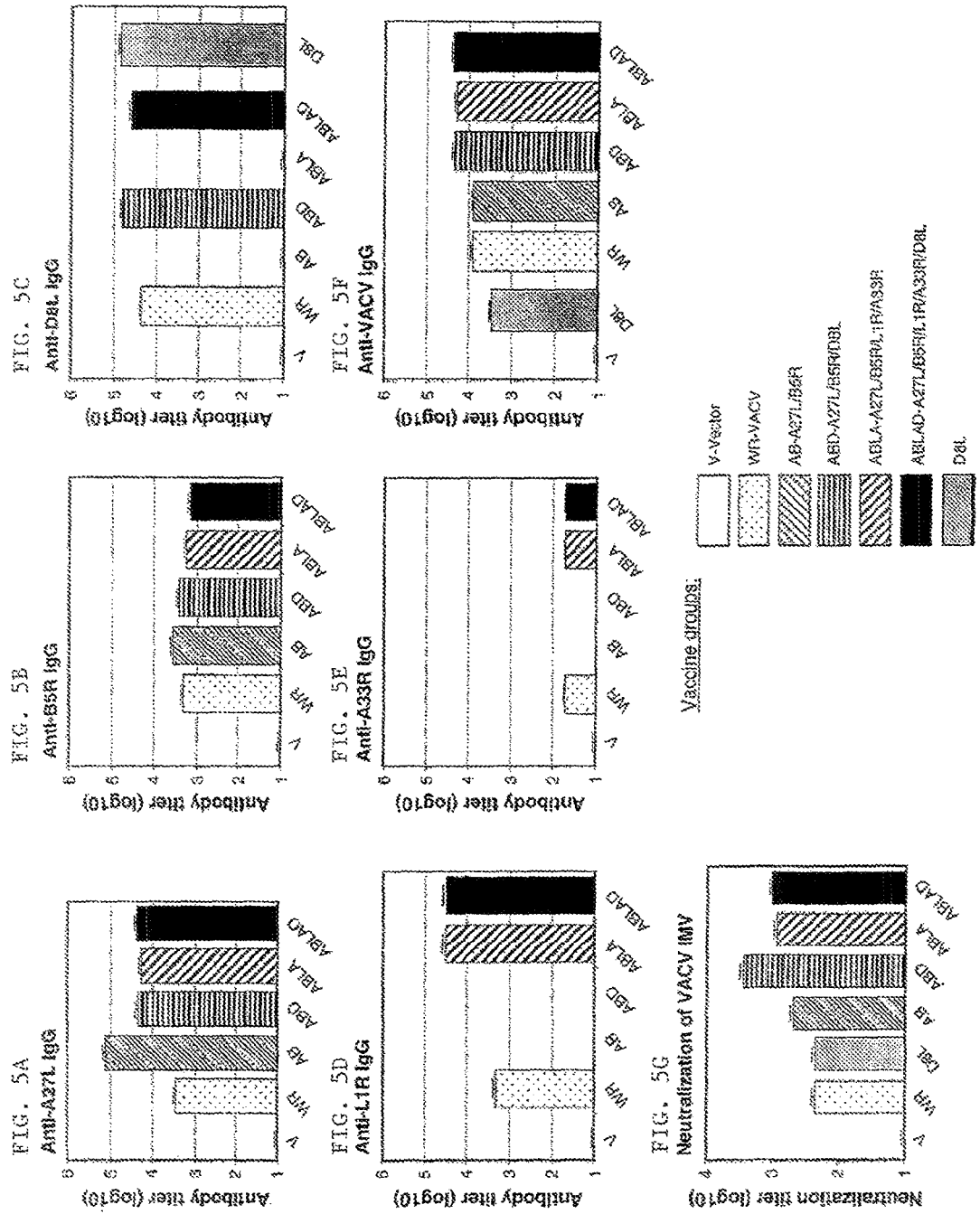

| | 25 | 40 | 77 | 110 | |
|---|---|---|---|---|---|
| A27-COP | ...ADK... | ...DEDDN... | ...DEV... | ... | (SEQ ID NO: 22) |
| A27-VACV | ...AAK... | ...DEDDN... | ...DEV... | ... | (SEQ ID NO: 23) |
| A31-Bangladesh1975 | ...AAK... | ...DGDDN... | ...DDV... | ... | (SEQ ID NO: 24) |
| A30-India1967 | ...AAK... | ...DGDNN... | ...DDV... | ... | (SEQ ID NO: 25) |

| | 40 | 50 53 | 82 | 95 102 | 132 136 | 145 | 152 | |
|---|---|---|---|---|---|---|---|---|
| B5-COP | ...NNKQ... | ...DQ.YHSSD... | ...YIS... | ...NSTMT.SCNGE... | ...QPL.LEH... | ...KEK... | ...EYMT... | (SEQ ID NOS: 26, 30, 34, 38, 42) |
| B5-VACV | ...NDKQ... | ...DQ.YHSSD... | ...YIS... | ...NSTMT.SCNGE... | ...QPL.LEH... | ...KEK... | ...EYMT... | (SEQ ID NOS: 27, 31, 35, 39, 43) |
| B6-Bangladesh1975 | ...NDKQ... | ...DS.YYSLD... | ...YVS... | ...NAIIT.ICKDE... | ...QSL.LDH... | ...KGK... | ...EHIT... | (SEQ ID NOS: 28, 32, 36, 40, 44) |
| B7-India1967 | ...NDKQ... | ...DS.YYSLD... | ...YVS... | ...NAIIT.ICKDE... | ...QSL.LDH... | ...KEK... | ...EHIT... | (SEQ ID NOS: 29, 33, 37, 41, 45) |

| | 170 | 188 | 216 | 238 | 248 | 304 | 317 | |
|---|---|---|---|---|---|---|---|---|
| B5-COP | ...ISC... | ...DIP... | ...FIL... | ...CVRTN... | ...VDD... | ...CDK... | ...LP | (SEQ ID NOS 46) |
| B5-VACV | ...ISC... | ...DMP... | ...FTL... | ...CVRTN... | ...VDD... | ...CDK... | ...LP | (SEQ ID NO: 47) |
| B6-Bangladesh1975 | ...ITC... | ...DIP... | ...FIL... | ...CIRSN... | ...VED... | ...CNK... | ...LL | (SEQ ID NO: 48) |
| B7-India1967 | ...ITC... | ...DIP... | ...FIL... | ...CIRSN... | ...VED... | ...CNK... | ...LL | (SEQ ID NO: 49) |

| | 2 | 24 | 52 | 124 | 143 | 158 | 163 | 175 |
|---|---|---|---|---|---|---|---|---|
| D8-COP | .PQ... | ...LDI... | ...YIS... | ...VSD... | ...RSA... | ...STL... | ...FTY... | ...IKH... |
| D8-VACV | .PQ... | ...LDI... | ...YIS... | ...VLD... | ...RSA... | ...SKL... | ...FTY... | ...INH... |
| F8-Bangladesh1975 | .SQ... | ...LNI... | ...YLS... | ...VSD... | ...RTA... | ...SKL... | ...FKY... | ...INH... |
| F8-India1967 | .SQ... | ...LNI... | ...YLS... | ...VSD... | ...RTA... | ...SKL... | ...FKY... | ...INH... |

| | 205 209 | 271 | 293 | 304 |
|---|---|---|---|---|
| D8-COP | ...SSS.HDG... | ...EGN... | ...FLM... | ... |
| D8-VACV | ...SSS.HDG... | ...EEN... | ...FFM... | ... |
| F8-Bangladesh1975 | ...SLS.HEG... | ...EGN... | ...FLM... | ... |
| F8-India1967 | ...SLS.HEG... | ...EGN... | ...FLM... | ... |

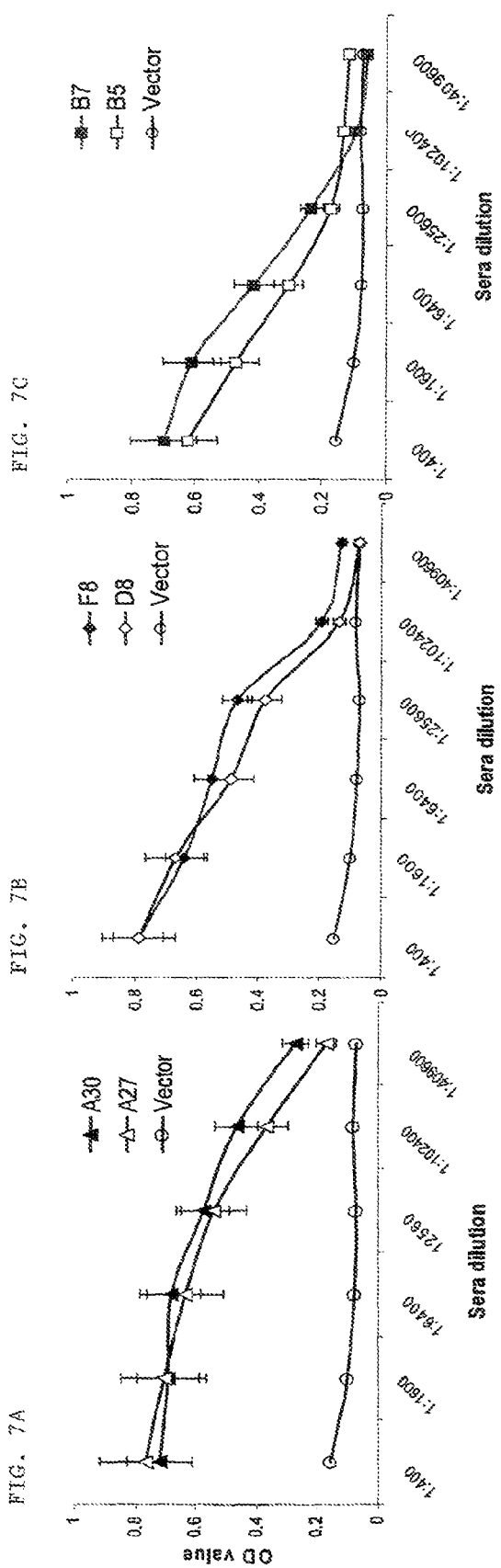

SEQUENCE LISTING

<160> NUMBER OF SEQ ID NOS: 49

<210> SEQ ID NO 1
<211> LENGTH: 915
<212> TYPE: DNA
<213> ORGANISM: Vaccinia virus

<400> SEQUENCE: 1

```
atgccgcaac aactatctcc tattaatata gaaactaaaa aagcaatttc taacgcgcga      60
ttgaagccgt tagacataca ttataatgag tcgaaaccaa ccactatcca gaacactgga     120
aaactagtaa ggattaattt taaggagga tatataagtg gagggtttct ccccaatgaa      180
tatgtgttat catcactaca tatatattgg ggaaaggaag acgattatgg atccaatcac     240
ttgatagatg tgtacaaata ctctggagag attaatcttg ttcattggaa taagaaaaaa     300
tatagttctt atgaagaggc aaaaaaacac gatgatggac ttatcattat ttctatattc     360
ttacaagtat tggatcataa aaatgtatat tttcaaaaga tagttaatca attggattcc     420
attagatccg ccaatacgtc tgcaccgttt gattcagtat tttatctaga caatttgctg     480
cctagtaagt tggattattt tacatatcta ggaacaacta tcaaccactc tgcagacgct     540
gtatggataa ttttccaac gccaataaac attcattctg atcaactatc taaattcaga    600
acactattgt cgtcgtctaa tcatgatgga aaaccgcatt atataacaga gaactataga     660
aatccgtata aattgaacga cgacacgcaa gtatattatt ctggggagat tatacgagca     720
gcaactacct ctccagcgcg cgagaactat tttatgagat ggttgtccga tttgagagag     780
acatgttttt catattatca aaaatatatc gaagagaata aaacattcgc aattattgcc     840
atagtattcg tgtttatact taccgctatt ctcttttta tgagtcgacg atattcgcga     900
gaaaaacaaa actag                                                     915
```

<210> SEQ ID NO 2
<211> LENGTH: 304
<212> TYPE: PRT
<213> ORGANISM: Vaccinia virus

<400> SEQUENCE: 2

```
Met Pro Gln Gln Leu Ser Pro Ile Asn Ile Glu Thr Lys Lys Ala Ile
 1               5                  10                  15

Ser Asn Ala Arg Leu Lys Pro Leu Asp Ile His Tyr Asn Glu Ser Lys
             20                  25                  30

Pro Thr Thr Ile Gln Asn Thr Gly Lys Leu Val Arg Ile Asn Phe Lys
         35                  40                  45

Gly Gly Tyr Ile Ser Gly Gly Phe Leu Pro Asn Glu Tyr Val Leu Ser
     50                  55                  60

Ser Leu His Ile Tyr Trp Gly Lys Glu Asp Tyr Gly Ser Asn His
 65                  70                  75                  80

Leu Ile Asp Val Tyr Lys Tyr Ser Gly Glu Ile Asn Leu Val His Trp
```

```
                    85                  90                  95
Asn Lys Lys Lys Tyr Ser Ser Tyr Glu Glu Ala Lys Lys His Asp Asp
            100                 105                 110
Gly Leu Ile Ile Ile Ser Ile Phe Leu Gln Val Leu Asp His Lys Asn
            115                 120                 125
Val Tyr Phe Gln Lys Ile Val Asn Gln Leu Asp Ser Ile Arg Ser Ala
            130                 135                 140
Asn Thr Ser Ala Pro Phe Asp Ser Val Phe Tyr Leu Asp Asn Leu Leu
145                 150                 155                 160
Pro Ser Lys Leu Asp Tyr Phe Thr Tyr Leu Gly Thr Thr Ile Asn His
                165                 170                 175
Ser Ala Asp Ala Val Trp Ile Ile Phe Pro Thr Pro Ile Asn Ile His
                180                 185                 190
Ser Asp Gln Leu Ser Lys Phe Arg Thr Leu Leu Ser Ser Ser Asn His
                195                 200                 205
Asp Gly Lys Pro His Tyr Ile Thr Glu Asn Tyr Arg Asn Pro Tyr Lys
            210                 215                 220
Leu Asn Asp Asp Thr Gln Val Tyr Tyr Ser Gly Glu Ile Ile Arg Ala
225                 230                 235                 240
Ala Thr Thr Ser Pro Ala Arg Glu Asn Tyr Phe Met Arg Trp Leu Ser
                245                 250                 255
Asp Leu Arg Glu Thr Cys Phe Ser Tyr Tyr Gln Lys Tyr Ile Glu Glu
                260                 265                 270
Asn Lys Thr Phe Ala Ile Ile Ala Ile Val Phe Val Phe Ile Leu Thr
            275                 280                 285
Ala Ile Leu Phe Phe Met Ser Arg Arg Tyr Ser Arg Glu Lys Gln Asn
            290                 295                 300
```

<210> SEQ ID NO 3
<211> LENGTH: 825
<212> TYPE: DNA
<213> ORGANISM: Artificial Sequence
<220> FEATURE:
<223> OTHER INFORMATION: Description of Artificial Sequence: Synthetic construct

<400> SEQUENCE: 3

| | | | | | |
|---|---|---|---|---|---|
| atgccgcaac | aactatctcc | tattaatata | gaaactaaaa | aagcaatttc | taacgcgcga | 60 |
| ttgaagccgt | tagacataca | ttataatgag | tcgaaaccaa | ccactatcca | gaacactgga | 120 |
| aaactagtaa | ggattaattt | taaaggagga | tatataagtg | gagggtttct | ccccaatgaa | 180 |
| tatgtgttat | catcactaca | tatatattgg | ggaaaggaag | acgattatgg | atccaatcac | 240 |
| ttgatagatg | tgtacaaata | ctctggagag | attaatcttg | tcattggaa | taagaaaaaa | 300 |
| tatagttctt | atgaagaggc | aaaaaaacac | gatgatggac | ttatcattat | ttctatattc | 360 |
| ttacaagtat | tggatcataa | aaatgtatat | tttcaaaaga | tagttaatca | attggattcc | 420 |
| attagatccg | ccaatacgtc | tgcaccgttt | gattcagtat | tttatctaga | caatttgctg | 480 |
| cctagtaagt | tggattattt | tacatatcta | ggaacaacta | tcaaccactc | tgcagacgct | 540 |
| gtatggataa | tttttccaac | gccaataaac | attcattctg | atcaactatc | taaattcaga | 600 |
| acactattgt | cgtcgtctaa | tcatgatgga | aaaccgcatt | atataacaga | aactatagaa | 660 |
| aatccgtata | aattgaacga | cgacacgcaa | gtatattatt | ctggggagat | tatacgagca | 720 |
| gcaactacct | ctccagcgcg | cgagaactat | tttatgagat | ggttgtccga | tttgagagag | 780 |
| acatgttttt | catattatca | aaaatatatc | gaagagaata | aaaca | | 825 |

<210> SEQ ID NO 4
<211> LENGTH: 275
<212> TYPE: PRT
<213> ORGANISM: Artificial Sequence
<220> FEATURE:
<223> OTHER INFORMATION: Description of Artificial Sequence: Synthetic construct

<400> SEQUENCE: 4

```
Met Pro Gln Gln Leu Ser Pro Ile Asn Ile Glu Thr Lys Lys Ala Ile
1               5                   10                  15

Ser Asn Ala Arg Leu Lys Pro Leu Asp Ile His Tyr Asn Glu Ser Lys
            20                  25                  30

Pro Thr Thr Ile Gln Asn Thr Gly Lys Leu Val Arg Ile Asn Phe Lys
        35                  40                  45

Gly Gly Tyr Ile Ser Gly Gly Phe Leu Pro Asn Glu Tyr Val Leu Ser
    50                  55                  60

Ser Leu His Ile Tyr Trp Gly Lys Glu Asp Asp Tyr Gly Ser Asn His
65                  70                  75                  80

Leu Ile Asp Val Tyr Lys Tyr Ser Gly Glu Ile Asn Leu Val His Trp
                85                  90                  95

Asn Lys Lys Lys Tyr Ser Ser Tyr Glu Glu Ala Lys Lys His Asp Asp
            100                 105                 110

Gly Leu Ile Ile Ile Ser Ile Phe Leu Gln Val Leu Asp His Lys Asn
        115                 120                 125

Val Tyr Phe Gln Lys Ile Val Asn Gln Leu Asp Ser Ile Arg Ser Ala
    130                 135                 140

Asn Thr Ser Ala Pro Phe Asp Ser Val Phe Tyr Leu Asp Asn Leu Leu
145                 150                 155                 160

Pro Ser Lys Leu Asp Tyr Phe Thr Tyr Leu Gly Thr Thr Ile Asn His
                165                 170                 175

Ser Ala Asp Ala Val Trp Ile Ile Phe Pro Thr Pro Ile Asn Ile His
            180                 185                 190

Ser Asp Gln Leu Ser Lys Phe Arg Thr Leu Leu Ser Ser Ser Asn His
        195                 200                 205

Asp Gly Lys Pro His Tyr Ile Thr Glu Asn Tyr Arg Asn Pro Tyr Lys
    210                 215                 220

Leu Asn Asp Asp Thr Gln Val Tyr Tyr Ser Gly Glu Ile Ile Arg Ala
225                 230                 235                 240

Ala Thr Thr Ser Pro Ala Arg Glu Asn Tyr Phe Met Arg Trp Leu Ser
                245                 250                 255

Asp Leu Arg Glu Thr Cys Phe Ser Tyr Tyr Gln Lys Tyr Ile Glu Glu
            260                 265                 270

Asn Lys Thr
        275
```

<210> SEQ ID NO 5
<211> LENGTH: 900
<212> TYPE: DNA
<213> ORGANISM: Artificial Sequence
<220> FEATURE:
<223> OTHER INFORMATION: Description of Artificial Sequence: Synthetic construct

<400> SEQUENCE: 5

```
atggatgcaa tgaagagagg gctctgctgt gtgctgctgc tgtgtggagc agtcttcgtt    60
```

```
tcggctagcc cgcaacaact atctcctatt aatatagaaa ctaaaaaagc aatttctaac      120
gcgcgattga agccgttaga catacattat aatgagtcga aaccaaccac tatccagaac      180
actggaaaac tagtaaggat taattttaaa ggaggatata aagtggagg gtttctcccc       240 aatgaatatg tgttatcatc actacatata tattgggaa aggaagacga ttatggatcc       300
aatcacttga tagatgtgta caaatactct ggagagatta atcttgttca ttggaataag      360
aaaaaatata gttcttatga gaggcaaaa aaacacgatg atggacttat cattatttct       420
atattcttac aagtattgga tcataaaaat gtatattttc aaaagatagt taatcaattg      480
gattccatta gatccgccaa tacgtctgca ccgtttgatt cagtatttta tctagacaat      540
ttgctgccta gtaagttgga ttattttaca tatctaggaa caactatcaa ccactctgca      600
gacgctgtat ggataatttt tccaacgcca ataaacattc attctgatca actatctaaa      660
ttcagaacac tattgtcgtc gtctaatcat gatggaaaac cgcattatat aacagagaac      720
tatagaaatc cgtataaatt gaacgacgac acgcaagtat attattctgg ggagattata      780
cgagcagcaa ctacctctcc agcgcgcgag aactatttta tgagatggtt gtccgatttg      840
agagagacat gttttcata ttatcaaaaa tatatcgaag agaataaaac attcgcatag       900
```

<210> SEQ ID NO 6
<211> LENGTH: 299
<212> TYPE: PRT
<213> ORGANISM: Artificial Sequence
<220> FEATURE:
<223> OTHER INFORMATION: Description of Artificial Sequence: Synthetic construct

<400> SEQUENCE: 6

```
Met Asp Ala Met Lys Arg Gly Leu Cys Cys Val Leu Leu Cys Gly
1               5                   10                  15

Ala Val Phe Val Ser Ala Ser Pro Gln Gln Leu Ser Pro Ile Asn Ile
            20                  25                  30

Glu Thr Lys Lys Ala Ile Ser Asn Ala Arg Leu Lys Pro Leu Asp Ile
        35                  40                  45

His Tyr Asn Glu Ser Lys Pro Thr Thr Ile Gln Asn Thr Gly Lys Leu
    50                  55                  60

Val Arg Ile Asn Phe Lys Gly Gly Tyr Ile Ser Gly Gly Phe Leu Pro
65                  70                  75                  80

Asn Glu Tyr Val Leu Ser Ser Leu His Ile Tyr Trp Gly Lys Glu Asp
                85                  90                  95

Asp Tyr Gly Ser Asn His Leu Ile Asp Val Tyr Lys Tyr Ser Gly Glu
            100                 105                 110

Ile Asn Leu Val His Trp Asn Lys Lys Tyr Ser Ser Tyr Glu Glu
        115                 120                 125

Ala Lys Lys His Asp Asp Gly Leu Ile Ile Ile Ser Ile Phe Leu Gln
    130                 135                 140

Val Leu Asp His Lys Asn Val Tyr Phe Gln Lys Ile Val Asn Gln Leu
145                 150                 155                 160

Asp Ser Ile Arg Ser Ala Asn Thr Ser Ala Pro Phe Asp Ser Val Phe
                165                 170                 175

Tyr Leu Asp Asn Leu Leu Pro Ser Lys Leu Asp Tyr Phe Thr Tyr Leu
            180                 185                 190

Gly Thr Thr Ile Asn His Ser Ala Asp Ala Val Trp Ile Ile Phe Pro
        195                 200                 205

Thr Pro Ile Asn Ile His Ser Asp Gln Leu Ser Lys Phe Arg Thr Leu
```

210                 215                 220
Leu Ser Ser Ser Asn His Asp Gly Lys Pro His Tyr Ile Thr Glu Asn
225                 230                 235                 240

Tyr Arg Asn Pro Tyr Lys Leu Asn Asp Asp Thr Gln Val Tyr Tyr Ser
            245                 250                 255

Gly Glu Ile Ile Arg Ala Ala Thr Thr Ser Pro Ala Arg Glu Asn Tyr
        260                 265                 270

Phe Met Arg Trp Leu Ser Asp Leu Arg Glu Thr Cys Phe Ser Tyr Tyr
            275                 280                 285

Gln Lys Tyr Ile Glu Glu Asn Lys Thr Phe Ala
        290                 295

<210> SEQ ID NO 7
<211> LENGTH: 333
<212> TYPE: DNA
<213> ORGANISM: Vaccinia virus

<400> SEQUENCE: 7
atggacggaa ctcttttccc cggagatgac gatcttgcaa ttccagcaac tgaattttt      60 tctacaaagg ctgctaaaaa gccagaggct aaacgcgaag caattgttaa agccgatgaa    120
gacgacaatg aggaaactct caaacaacgg ctaactaatt tggaaaaaaa gattactaat    180
gtaacaacaa agtttgaaca aatagaaaag tgttgtaaac gcaacgatga agttctattt    240
aggttggaaa atcacgctga aactctaaga gcggctatga tatctctggc taaaaagatt    300
gatgttcaga ctggacggcg cccatatgag taa                                 333

<210> SEQ ID NO 8
<211> LENGTH: 110
<212> TYPE: PRT
<213> ORGANISM: Vaccinia virus

<400> SEQUENCE: 8

Met Asp Gly Thr Leu Phe Pro Gly Asp Asp Leu Ala Ile Pro Ala
1               5                   10                  15

Thr Glu Phe Phe Ser Thr Lys Ala Ala Lys Lys Pro Glu Ala Lys Arg
            20                  25                  30

Glu Ala Ile Val Lys Ala Asp Glu Asp Asp Asn Glu Glu Thr Leu Lys
        35                  40                  45

Gln Arg Leu Thr Asn Leu Glu Lys Lys Ile Thr Asn Val Thr Thr Lys
    50                  55                  60

Phe Glu Gln Ile Glu Lys Cys Cys Lys Arg Asn Asp Glu Val Leu Phe
65                  70                  75                  80

Arg Leu Glu Asn His Ala Glu Thr Leu Arg Ala Ala Met Ile Ser Leu
                85                  90                  95

Ala Lys Lys Ile Asp Val Gln Thr Gly Arg Arg Pro Tyr Glu
            100                 105                 110

<210> SEQ ID NO 9
<211> LENGTH: 954
<212> TYPE: DNA
<213> ORGANISM: Vaccinia virus

<400> SEQUENCE: 9
atgaaaacga tttccgttgt tacgttgtta tgcgtactac ctgctgttgt ttattcaaca     60
tgtactgtac ccactatgaa taacgctaaa ttaacgtcta ccgaaacatc gtttaatgat    120
aaacagaaag ttacgtttac atgtgatcag ggatatcatt cttcggatcc aaatgctgtc    180

```
tgcgaaacag ataaatggaa atacgaaaat ccatgcaaaa aaatgtgcac agtttctgat    240
tacatctctg aattatataa taaaccgcta tacgaagtga attccaccat gacactaagt    300
tgcaacggcg aaacaaaata ttttcgttgc gaagaaaaaa atggaaatac ttcttggaat    360
gatactgtta cgtgtcctaa tgcggaatgt caacctcttc aattagaaca cggatcgtgt    420
caaccagtta agaaaaaata ctcatttggg gaatatatga ctatcaactg tgatgttgga    480
tatgaggtta ttggtgcttc gtacataagt tgtacagcta attcttggaa tgttattcca    540
tcatgtcaac aaaaatgtga tatgccgtct ctatctaatg gattaatttc cggatctaca    600
ttttctatcg gtggcgttat acatcttagt tgtaaaagtg gttttacact aacggggtct    660
ccatcatcca catgtatcga cggtaaatgg aatcccgtac tcccaatatg tgtacgaact    720
aacgaagaat ttgatccagt ggatgatggt cccgacgatg agacagattt gagcaaactc    780
tcgaaagacg ttgtacaata tgaacaagaa atagaatcgt tagaagcaac ttatcatata    840
atcatagtgg cgttaacaat tatgggcgtc atattttaa tctccgttat agtattagtt    900
tgttcctgtg acaaaaataa tgaccaatat aagttccata aattgctacc gtaa         954
```

```
<210> SEQ ID NO 10
<211> LENGTH: 317
<212> TYPE: PRT
<213> ORGANISM: Vaccinia virus

<400> SEQUENCE: 10

Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr
            20                  25                  30

Ser Thr Glu Thr Ser Phe Asn Asp Lys Gln Lys Val Thr Phe Thr Cys
        35                  40                  45

Asp Gln Gly Tyr His Ser Ser Asp Pro Asn Ala Val Cys Glu Thr Asp
    50                  55                  60

Lys Trp Lys Tyr Glu Asn Pro Cys Lys Lys Met Cys Thr Val Ser Asp
65                  70                  75                  80

Tyr Ile Ser Glu Leu Tyr Asn Lys Pro Leu Tyr Glu Val Asn Ser Thr
                85                  90                  95

Met Thr Leu Ser Cys Asn Gly Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Pro Leu Gln Leu Glu His Gly Ser Cys Gln Pro Val Lys
    130                 135                 140

Glu Lys Tyr Ser Phe Gly Glu Tyr Met Thr Ile Asn Cys Asp Val Gly
145                 150                 155                 160

Tyr Glu Val Ile Gly Ala Ser Tyr Ile Ser Cys Thr Ala Asn Ser Trp
                165                 170                 175

Asn Val Ile Pro Ser Cys Gln Gln Lys Cys Asp Met Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Thr Leu Thr Gly Ser Pro Ser Ser Thr
    210                 215                 220

Cys Ile Asp Gly Lys Trp Asn Pro Val Leu Pro Ile Cys Val Arg Thr
225                 230                 235                 240
```

-continued

```
Asn Glu Glu Phe Asp Pro Val Asp Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Ala Thr Tyr His Ile Ile Ile Val Ala Leu Thr Ile Met
        275                 280                 285

Gly Val Ile Phe Leu Ile Ser Val Ile Val Leu Val Cys Ser Cys Asp
    290                 295                 300

Lys Asn Asn Asp Gln Tyr Lys Phe His Lys Leu Leu Pro
305                 310                 315

<210> SEQ ID NO 11
<211> LENGTH: 753
<212> TYPE: DNA
<213> ORGANISM: Vaccinia virus
<400> SEQUENCE: 11
atgggtgccg cggcaagcat acagacgacg gtgaatacac tcagcgaacg tatctcgtct      60
aaattagaac aagaagcgaa tgctagtgct caaacaaaat gtgatataga aatcggaaat     120
ttttatatcc gacaaaacca tggatgtaac ctcactgtta aaaatatgtg ctctgcggac     180
gcggatgctc agttggatgc tgtgttatca gccgctacag aaacatatag tggattaaca     240
ccggaacaaa aagcatacgt gccagctatg tttactgctg cgttaaacat tcagacgagt     300
gtaaacactg ttgttagaga ttttgaaaat tatgtgaaac agacttgtaa ttctagcgcg     360
gtcgtcgata acaaattaaa gatacaaaac gtaatcatag atgaatgtta cggagcccca     420
ggatctccaa caaatttgga atttattaat acaggatcta gcaaaggaaa ttgtgccatt     480
aaggcgttga tgcaattgac gactaaggcc actactcaaa tagcacctaa acaagttgct     540
ggtacaggag ttcagtttta tatgattgtt atcggtgtta taatattggc agcgttgttt     600
atgtactatg ccaagcgtat gttgttcaca tccaccaatg ataaaatcaa acttatttta     660
gccaataagg aaaacgtcca ttggactact tacatggaca cattctttag aacttctccg     720
atggttattg ctaccacgga tatgcaaaac tga                                  753

<210> SEQ ID NO 12
<211> LENGTH: 250
<212> TYPE: PRT
<213> ORGANISM: Vaccinia virus
<400> SEQUENCE: 12

Met Gly Ala Ala Ala Ser Ile Gln Thr Thr Val Asn Thr Leu Ser Glu
1               5                   10                  15

Arg Ile Ser Ser Lys Leu Glu Gln Glu Ala Asn Ala Ser Ala Gln Thr
            20                  25                  30

Lys Cys Asp Ile Glu Ile Gly Asn Phe Tyr Ile Arg Gln Asn His Gly
        35                  40                  45

Cys Asn Leu Thr Val Lys Asn Met Cys Ser Ala Asp Ala Asp Ala Gln
    50                  55                  60

Leu Asp Ala Val Leu Ser Ala Ala Thr Glu Thr Tyr Ser Gly Leu Thr
65                  70                  75                  80

Pro Glu Gln Lys Ala Tyr Val Pro Ala Met Phe Thr Ala Ala Leu Asn
                85                  90                  95

Ile Gln Thr Ser Val Asn Thr Val Val Arg Asp Phe Glu Asn Tyr Val
            100                 105                 110
```

```
Lys Gln Thr Cys Asn Ser Ser Ala Val Val Asp Asn Lys Leu Lys Ile
        115                 120                 125

Gln Asn Val Ile Ile Asp Glu Cys Tyr Gly Ala Pro Gly Ser Pro Thr
    130                 135                 140

Asn Leu Glu Phe Ile Asn Thr Gly Ser Ser Lys Gly Asn Cys Ala Ile
145                 150                 155                 160

Lys Ala Leu Met Gln Leu Thr Thr Lys Ala Thr Thr Gln Ile Ala Pro
                165                 170                 175

Lys Gln Val Ala Gly Thr Gly Val Gln Phe Tyr Met Ile Val Ile Gly
            180                 185                 190

Val Ile Ile Leu Ala Ala Leu Phe Met Tyr Tyr Ala Lys Arg Met Leu
        195                 200                 205

Phe Thr Ser Thr Asn Asp Lys Ile Lys Leu Ile Leu Ala Asn Lys Glu
    210                 215                 220

Asn Val His Trp Thr Thr Tyr Met Asp Thr Phe Phe Arg Thr Ser Pro
225                 230                 235                 240

Met Val Ile Ala Thr Thr Asp Met Gln Asn
                245                 250

<210> SEQ ID NO 13
<211> LENGTH: 558
<212> TYPE: DNA
<213> ORGANISM: Vaccinia virus

<400> SEQUENCE: 13
atgatgacac cagaaaacga cgaagagcag acatctgtgt tctccgctac tgtttacgga      60
gacaaaattc aaggaaagaa taaacgcaaa cgcgtgattg gtctatgtat tagaatatct     120
atggttattt cactactatc tatgattacc atgtccgcgt ttctcatagt gcgcctaaat     180
caatgcatgt ctgctaacga ggctgctatt actgacgccg ctgttgccgt tgctgctgca     240
tcatctactc atagaaaggt tgcgtctagc actacacaat atgatcacaa agaaagctgt     300
aatggtttat attaccaggg ttcttgttat atattacatt cagactacca gttattctcg     360
gatgctaaag caaattgcac tgcggaatca tcaacactac ccataaaatc cgatgtcttg     420
attacctggc tcattgatta tgttgaggat acatggggat ctgatggtaa tccaattaca     480
aaaactacat ccgattatca agattctgat gtatcacaag aagttagaaa gtattttgt      540 gttaaaacaa tgaactaa                                                   558

<210> SEQ ID NO 14
<211> LENGTH: 185
<212> TYPE: PRT
<213> ORGANISM: Vaccinia virus

<400> SEQUENCE: 14

Met Met Thr Pro Glu Asn Asp Glu Glu Gln Thr Ser Val Phe Ser Ala
1               5                   10                  15

Thr Val Tyr Gly Asp Lys Ile Gln Gly Lys Asn Lys Arg Lys Arg Val
            20                  25                  30

Ile Gly Leu Cys Ile Arg Ile Ser Met Val Ile Ser Leu Leu Ser Met
        35                  40                  45

Ile Thr Met Ser Ala Phe Leu Ile Val Arg Leu Asn Gln Cys Met Ser
    50                  55                  60

Ala Asn Glu Ala Ala Ile Thr Asp Ala Ala Val Ala Val Ala Ala Ala
65                  70                  75                  80

Ser Ser Thr His Arg Lys Val Ala Ser Ser Thr Thr Gln Tyr Asp His
```

-continued

```
                    85                  90                  95
Lys Glu Ser Cys Asn Gly Leu Tyr Tyr Gln Gly Ser Cys Tyr Ile Leu
                100                 105                 110

His Ser Asp Tyr Gln Leu Phe Ser Asp Ala Lys Ala Asn Cys Thr Ala
            115                 120                 125

Glu Ser Ser Thr Leu Pro Asn Lys Ser Asp Val Leu Ile Thr Trp Leu
        130                 135                 140

Ile Asp Tyr Val Glu Asp Thr Trp Gly Ser Asp Gly Asn Pro Ile Thr
145                 150                 155                 160

Lys Thr Thr Ser Asp Tyr Gln Asp Ser Asp Val Ser Gln Glu Val Arg
                165                 170                 175

Lys Tyr Phe Cys Val Lys Thr Met Asn
            180                 185

<210> SEQ ID NO 15
<211> LENGTH: 933
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 15
ctgcaggcta gcatgagcca gcaactgagc cccatcaaca tcgagaccaa gaaggccatc        60
agcaacgcac gcctgaagcc cctgaacatc cactacaacg agagcaagcc caccaccatc       120
cagaacaccg gcaagctggt gcgcatcaac ttcaagggag gctacctgag cggaggcttc       180
cttcccaacg agtacgtgct gagcagcctg cacatctact ggggcaagga ggatgactac       240
ggcagcaacc acctgatcga cgtgtacaag tacagcggcg agatcaacct ggtgcactgg       300
aacaagaaga agtacagcag ctacgaggaa gccaagaagc acgacgatgg cctgatcatc       360
atcagcatct tccttcaggt gagcgaccac aagaacgtgt acttccagaa gatcgtgaac       420
caactggaca gcatccgcac tgccaacacc agcgctccct tcgacagcgt gttctacctg       480
gacaacctgc tgcccagcaa gctggactac ttcaagtacc taggcaccac catcaaccac       540
agtgccgacg ccgtgtggat catctttccc accectatca acatccacag cgaccaactg       600
agcaagttcc gcaccctgct gagcctgagc aaccatgagg gcaagcccca ctacatcacc       660
gagaactacc gcaatcccta aagctgaac gacgataccg aggtgtacta cagtggcgag       720
atcatccgag ccgccaccac cagccctgct cgcgagaact acttcatgcg ctggctgagc       780
gacctgcgcg agacctgctt cagctactac cagaagtaca tcgagggcaa caagaccttc       840
gccatcatcg ccatcgtgtt cgtgtacatc ctgaccgcca tcctgttcct gatgagccgc       900
cgatacagcc gcgagaagca gaactaagga tcc                                   933

<210> SEQ ID NO 16
<211> LENGTH: 304
<212> TYPE: PRT
<213> ORGANISM: Variola major virus

<400> SEQUENCE: 16

Met Ser Gln Gln Leu Ser Pro Ile Asn Ile Glu Thr Lys Lys Ala Ile
1               5                   10                  15

Ser Asn Ala Arg Leu Lys Pro Leu Asn Ile His Tyr Asn Glu Ser Lys
            20                  25                  30

Pro Thr Thr Ile Gln Asn Thr Gly Lys Leu Val Arg Ile Asn Phe Lys
        35                  40                  45
```

-continued

```
Gly Gly Tyr Leu Ser Gly Gly Phe Leu Pro Asn Glu Tyr Val Leu Ser
     50                  55                  60

Ser Leu His Ile Tyr Trp Gly Lys Glu Asp Tyr Gly Ser Asn His
 65                  70                  75                  80

Leu Ile Asp Val Tyr Lys Tyr Ser Gly Glu Ile Asn Leu Val His Trp
                 85                  90                  95

Asn Lys Lys Tyr Ser Ser Tyr Glu Glu Ala Lys Lys His Asp Asp
             100                 105                 110

Gly Leu Ile Ile Ile Ser Ile Phe Leu Gln Val Ser Asp His Lys Asn
             115                 120                 125

Val Tyr Phe Gln Lys Ile Val Asn Gln Leu Asp Ser Ile Arg Thr Ala
         130                 135                 140

Asn Thr Ser Ala Pro Phe Asp Ser Val Phe Tyr Leu Asp Asn Leu Leu
145                 150                 155                 160

Pro Ser Lys Leu Asp Tyr Phe Lys Tyr Leu Gly Thr Thr Ile Asn His
                 165                 170                 175

Ser Ala Asp Ala Val Trp Ile Ile Phe Pro Thr Pro Ile Asn Ile His
             180                 185                 190

Ser Asp Gln Leu Ser Lys Phe Arg Thr Leu Leu Ser Leu Ser Asn His
         195                 200                 205

Glu Gly Lys Pro His Tyr Ile Thr Glu Asn Tyr Arg Asn Pro Tyr Lys
     210                 215                 220

Leu Asn Asp Asp Thr Glu Val Tyr Tyr Ser Gly Glu Ile Ile Arg Ala
225                 230                 235                 240

Ala Thr Thr Ser Pro Ala Arg Glu Asn Tyr Phe Met Arg Trp Leu Ser
                 245                 250                 255

Asp Leu Arg Glu Thr Cys Phe Ser Tyr Tyr Gln Lys Tyr Ile Glu Gly
             260                 265                 270

Asn Lys Thr Phe Ala Ile Ile Ala Ile Val Phe Val Tyr Ile Leu Thr
         275                 280                 285

Ala Ile Leu Phe Leu Met Ser Arg Arg Tyr Ser Arg Glu Lys Gln Asn
     290                 295                 300
```

<210> SEQ ID NO 17
<211> LENGTH: 351
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 17

```
ctgcaggcta gcatggacgg caccctgttc cctggcgacg acgacctggc catccccgcc      60
accgagttct tcagcaccaa ggctgccaag aagcctgagg ccaagcgcga ggccatcgtg     120
aaggctgacg cgacaacaa cgaggagacc ctgaagcagc gcctgaccaa cctggagaag     180
aagatcacca acgtgaccac caagttcgag cagatcgaga gtgctgcaa gcgcaacgac     240 gacgtgctgt tccgcctgga gaaccacgcc gagaccctgc gcgctgccat gatcagcctg     300
gccaagaaga tcgacgtgca gactggcaga cgcccctacg agtaaggatc c              351
```

<210> SEQ ID NO 18
<211> LENGTH: 110
<212> TYPE: PRT
<213> ORGANISM: Variola major virus

<400> SEQUENCE: 18

Met Asp Gly Thr Leu Phe Pro Gly Asp Asp Leu Ala Ile Pro Ala
1               5                   10                  15

Thr Glu Phe Phe Ser Thr Lys Ala Ala Lys Lys Pro Glu Ala Lys Arg
                20                  25                  30

Glu Ala Ile Val Lys Ala Asp Gly Asp Asn Asn Glu Glu Thr Leu Lys
            35                  40                  45

Gln Arg Leu Thr Asn Leu Glu Lys Lys Ile Thr Asn Val Thr Thr Lys
        50                  55                  60

Phe Glu Gln Ile Glu Lys Cys Cys Lys Arg Asn Asp Asp Val Leu Phe
65                  70                  75                  80

Arg Leu Glu Asn His Ala Glu Thr Leu Arg Ala Ala Met Ile Ser Leu
                85                  90                  95

Ala Lys Lys Ile Asp Val Gln Thr Gly Arg Arg Pro Tyr Glu
            100                 105                 110

<210> SEQ ID NO 19
<211> LENGTH: 966
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 19
ctgcagatga agaccatcag cgtggtgacc ctgctgtgcg tgcttcctgc cgtggtgtac      60
agcacctgca ccgtgccrac catgaacaac gccaagctga ccagcaccga gaccagcttc     120
aacgacaagc agaaagtgac cttcacctgc gacagcggct actacagcct ggaccccaac     180
gctgtgtgcg agaccgacaa gtggaagtac gagaatccct gcaagaagat gtgcaccgtg     240
agcgactacg tgagcgagct gtacaacaaa ccoctgtacg aggtgaacgc tatcatcacc     300
ctgatctgca aggacgagac caagtacttc cgctgcgagg agaagaatgg caacaccagc     360
tggaacgaca ccgtgacctg ccccaacgct gagtgccaga gcctccagct ggaccacggc     420
agctgccagc ccgtgaagga agtacagc ttcggcgagc acatcaccat caactgcgac       480
gtgggctacg aggtgatcgg tgccagctac atcacctgca ccgctaacag ctggaacgtg     540
atcccragct gccagcagaa gtgcgacatt cccagcctga caacggcct gatcagtggc      600 agcaccttca gcatcggtgg cgtgatccac ctgagctgca agagcggctt catcctgact     660
ggcagtccca gcagcacctg catcgacggc aagtggaacc ctgtgcttcc catctgcatc     720
cgcagcaacg aggagttcga ccccgtggag gacggtcccg acgacgagac cgacctgagc     780
aagctgagca agacgtggt gcagtacgag caggagatcg agagccttga ggctaccctac     840 cacatcatta tcgtggctct gaccatcatg ggcgtgatct tcctgatcag cgtgatcgtg     900
ctggtgtgca gctgcaacaa gaacaacgac cagtacaagt ccacaagct gcttctgtaa      960 ggatcc                                                               966

<210> SEQ ID NO 20
<211> LENGTH: 317
<212> TYPE: PRT
<213> ORGANISM: Variola major virus

<400> SEQUENCE: 20

Met Lys Thr Ile Ser Val Val Thr Leu Leu Cys Val Leu Pro Ala Val
1               5                   10                  15

Val Tyr Ser Thr Cys Thr Val Pro Thr Met Asn Asn Ala Lys Leu Thr

```
                20                  25                  30
Ser Thr Glu Thr Ser Phe Asn Asp Lys Gln Lys Val Thr Phe Thr Cys
            35                  40                  45

Asp Ser Gly Tyr Tyr Ser Leu Asp Pro Asn Ala Val Cys Glu Thr Asp
        50                  55                  60

Lys Trp Lys Tyr Glu Asn Pro Cys Lys Lys Met Cys Thr Val Ser Asp
65                  70                  75                  80

Tyr Val Ser Glu Leu Tyr Asn Lys Pro Leu Tyr Glu Val Asn Ala Ile
                85                  90                  95

Ile Thr Leu Ile Cys Lys Asp Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Ser Leu Gln Leu Asp His Gly Ser Cys Gln Pro Val Lys
    130                 135                 140

Glu Lys Tyr Ser Phe Gly Glu His Ile Thr Ile Asn Cys Asp Val Gly
145                 150                 155                 160

Tyr Glu Val Ile Gly Ala Ser Tyr Ile Thr Cys Thr Ala Asn Ser Trp
                165                 170                 175

Asn Val Ile Pro Ser Cys Gln Gln Lys Cys Asp Ile Pro Ser Leu Ser
            180                 185                 190

Asn Gly Leu Ile Ser Gly Ser Thr Phe Ser Ile Gly Val Ile His
        195                 200                 205

Leu Ser Cys Lys Ser Gly Phe Ile Leu Thr Gly Ser Pro Ser Ser Thr
    210                 215                 220

Cys Ile Asp Gly Lys Trp Asn Pro Val Leu Pro Ile Cys Ile Arg Ser
225                 230                 235                 240

Asn Glu Glu Phe Asp Pro Val Glu Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Ala Thr Tyr His Ile Ile Ile Val Ala Leu Thr Ile Met
        275                 280                 285

Gly Val Ile Phe Leu Ile Ser Val Ile Val Leu Val Cys Ser Cys Asn
    290                 295                 300

Lys Asn Asn Asp Gln Tyr Lys Phe His Lys Leu Leu Leu
305                 310                 315

<210> SEQ ID NO 21
<211> LENGTH: 23
<212> TYPE: PRT
<213> ORGANISM: Homo sapiens

<400> SEQUENCE: 21

Met Asp Ala Met Lys Arg Gly Leu Cys Cys Val Leu Leu Leu Cys Gly
1               5                   10                  15

Ala Val Phe Val Ser Ala Ser
            20

<210> SEQ ID NO 22
<211> LENGTH: 5
<212> TYPE: PRT
<213> ORGANISM: Vaccinia virus Copenhagen

<400> SEQUENCE: 22

Asp Glu Asp Asp Asn
```

-continued

```
<210> SEQ ID NO 23
<211> LENGTH: 5
<212> TYPE: PRT
<213> ORGANISM: Vaccinia virus Western Reserve

<400> SEQUENCE: 23

Asp Glu Asp Asp Asn
1               5

<210> SEQ ID NO 24
<211> LENGTH: 5
<212> TYPE: PRT
<213> ORGANISM: Variola major virus Bangladesh 1975

<400> SEQUENCE: 24

Asp Gly Asp Asp Asn
1               5

<210> SEQ ID NO 25
<211> LENGTH: 5
<212> TYPE: PRT
<213> ORGANISM: Variola major virus India 1967

<400> SEQUENCE: 25

Asp Gly Asp Asn Asn
1               5

<210> SEQ ID NO 26
<211> LENGTH: 4
<212> TYPE: PRT
<213> ORGANISM: Vaccinia virus Copenhagen

<400> SEQUENCE: 26

Asn Asn Lys Gln
1

<210> SEQ ID NO 27
<211> LENGTH: 4
<212> TYPE: PRT
<213> ORGANISM: Vaccinia virus Western Reserve

<400> SEQUENCE: 27

Asn Asp Lys Gln
1

<210> SEQ ID NO 28
<211> LENGTH: 4
<212> TYPE: PRT
<213> ORGANISM: Variola major virus Bangladesh 1975

<400> SEQUENCE: 28

Asn Asp Lys Gln
1

<210> SEQ ID NO 29
<211> LENGTH: 4
<212> TYPE: PRT
<213> ORGANISM: Variola major virus India 1967

<400> SEQUENCE: 29

Asn Asp Lys Gln
1
```

```
<210> SEQ ID NO 30
<211> LENGTH: 5
<212> TYPE: PRT
<213> ORGANISM: Vaccinia virus Copenhagen

<400> SEQUENCE: 30

Tyr His Ser Ser Asp
1               5

<210> SEQ ID NO 31
<211> LENGTH: 5
<212> TYPE: PRT
<213> ORGANISM: Vaccinia virus Western Reserve

<400> SEQUENCE: 31

Tyr His Ser Ser Asp
1               5

<210> SEQ ID NO 32
<211> LENGTH: 5
<212> TYPE: PRT
<213> ORGANISM: Variola major virus Bangladesh 1975

<400> SEQUENCE: 32

Tyr Tyr Ser Leu Asp
1               5

<210> SEQ ID NO 33
<211> LENGTH: 5
<212> TYPE: PRT
<213> ORGANISM: Variola major virus India 1967

<400> SEQUENCE: 33

Tyr Tyr Ser Leu Asp
1               5

<210> SEQ ID NO 34
<211> LENGTH: 5
<212> TYPE: PRT
<213> ORGANISM: Vaccinia virus Copenhagen

<400> SEQUENCE: 34

Asn Ser Thr Met Thr
1               5

<210> SEQ ID NO 35
<211> LENGTH: 5
<212> TYPE: PRT
<213> ORGANISM: Vaccinia virus Western Reserve

<400> SEQUENCE: 35

Asn Ser Thr Met Thr
1               5

<210> SEQ ID NO 36
<211> LENGTH: 5
<212> TYPE: PRT
<213> ORGANISM: Variola major virus Bangladesh 1975

<400> SEQUENCE: 36

Asn Ala Ile Ile Thr
1               5

<210> SEQ ID NO 37
```

```
<211> LENGTH: 5
<212> TYPE: PRT
<213> ORGANISM: Variola major virus India 1967

<400> SEQUENCE: 37

Asn Ala Ile Ile Thr
1               5

<210> SEQ ID NO 38
<211> LENGTH: 5
<212> TYPE: PRT
<213> ORGANISM: Vaccinia virus Copenhagen

<400> SEQUENCE: 38

Ser Cys Asn Gly Glu
1               5

<210> SEQ ID NO 39
<211> LENGTH: 5
<212> TYPE: PRT
<213> ORGANISM: Vaccinia virus Western Reserve

<400> SEQUENCE: 39

Ser Cys Asn Gly Glu
1               5

<210> SEQ ID NO 40
<211> LENGTH: 5
<212> TYPE: PRT
<213> ORGANISM: Variola major virus Bangladesh 1975

<400> SEQUENCE: 40

Ile Cys Lys Asp Glu
1               5

<210> SEQ ID NO 41
<211> LENGTH: 5
<212> TYPE: PRT
<213> ORGANISM: Variola major virus India 1967

<400> SEQUENCE: 41

Ile Cys Lys Asp Glu
1               5

<210> SEQ ID NO 42
<211> LENGTH: 4
<212> TYPE: PRT
<213> ORGANISM: Vaccinia virus Copenhagen

<400> SEQUENCE: 42

Glu Tyr Met Thr
1

<210> SEQ ID NO 43
<211> LENGTH: 4
<212> TYPE: PRT
<213> ORGANISM: Vaccinia virus Western Reserve

<400> SEQUENCE: 43

Glu Tyr Met Thr
1

<210> SEQ ID NO 44
<211> LENGTH: 4
<212> TYPE: PRT
```

-continued

```
<213> ORGANISM: Variola major virus Bangladesh 1975

<400> SEQUENCE: 44

Glu His Ile Thr
1

<210> SEQ ID NO 45
<211> LENGTH: 4
<212> TYPE: PRT
<213> ORGANISM: Variola major virus India 1967

<400> SEQUENCE: 45

Glu His Ile Thr
1

<210> SEQ ID NO 46
<211> LENGTH: 5
<212> TYPE: PRT
<213> ORGANISM: Vaccinia virus Copenhagen

<400> SEQUENCE: 46

Cys Val Arg Thr Asn
1               5

<210> SEQ ID NO 47
<211> LENGTH: 5
<212> TYPE: PRT
<213> ORGANISM: Vaccinia virus Western Reserve

<400> SEQUENCE: 47

Cys Val Arg Thr Asn
1               5

<210> SEQ ID NO 48
<211> LENGTH: 5
<212> TYPE: PRT
<213> ORGANISM: Variola major virus Bangladesh 1975

<400> SEQUENCE: 48

Cys Ile Arg Ser Asn
1               5

<210> SEQ ID NO 49
<211> LENGTH: 5
<212> TYPE: PRT
<213> ORGANISM: Variola major virus India 1967

<400> SEQUENCE: 49

Cys Ile Arg Ser Asn
1               5
```

POXVIRUS METHODS AND COMPOSITIONS

STATEMENT AS TO FEDERALLY SPONSORED RESEARCH

The work described herein was funded, in part, through a grant from the National Institutes of Health (Grant No. AI057159 awarded to Shan Lu). The United States government may, therefore, have certain rights in the invention.

TECHNICAL FIELD

This invention relates to methods and compositions for inducing immune responses, and more particularly to methods and compositions for inducing immune responses to viruses.

BACKGROUND

Poxviruses, which include variola major (VARV), vaccinia virus (VACV), monkeypox, ectromelia virus (ECTV) and others, belong to the *orthopoxvirus* genus. Poxviruses are large, complex viruses. A poxvirus genome encodes about 200 proteins. The complexity of poxviruses has, in part, delayed the identification of protective antigens. On the other hand, considerable cross-protection has been observed between *orthopox* viruses. For example, vaccination with live attenuated vaccinia virus protects from infection by variola major, the virus that causes smallpox. The original smallpox vaccine, based on live attenuated vaccinia, eradicated smallpox from the worldwide human population with the last case of natural smallpox infection occurring in Somalia in 1977 (Radetsky, 1999, Pediat. Inf. Dis. J., 18:85-93). Production of the live, attenuated vaccinia approved for use as a smallpox vaccine in the United States, DryVax™ (Wyeth Laboratories, Inc.) was discontinued in 1982. Adverse events associated with vaccination with the live attenuated virus vaccine include progressive vaccinia, eczema, post-vaccinial encephalitis, and myocarditis (Casey et al., 2005, JAMA, 294(21):2734-43; Belongia et al., 2003, Clin. Med. Res., 1(2):87-92). Despite safety concerns, live vaccinia virus remains the main form of smallpox vaccine. A new generation of live attenuated vaccinia virus vaccines are being produced in cultured cells for stockpiling in hopes that the supply will be available to protect the general population in the event of a bioterrorist attack, as the majority of the world's population no longer has immunity to smallpox (Artenstein et al., 2005, Vaccine, 23(25):3301-9; Fang et al., 2006, Virology 345(1): 231-43; Monath et al., 2004, Int. J. Infect. Dis., 8 (Suppl 2):S31-44).

SUMMARY

The compositions described herein provide novel forms of poxvirus antigens, combinations of antigens, and nucleic acid sequences encoding the antigens that provide potent protection against infection. The compositions include poxvirus antigens (e.g., vaccinia virus and variola virus antigens) and nucleic acids encoding the antigens that are modified so as to be more immunogenic. Modifications that enhance immunogenicity include truncation (e.g., to remove hydrophobic regions), addition of a heterologous signal sequence, and codon optimization. For example, it has been discovered that expression of a truncated form of vaccinia D8 lacking a transmembrane domain and cytoplasmic tail in association with a heterologous signal sequence enhances its immunogenicity relative to a wild type form of D8. Codon optimization of poxvirus sequences permits enhanced expression in mammalian as well as bacterial cells, which is beneficial for use in a DNA vaccine, and for recombinant production of the pox antigens.

In addition, it has been discovered that certain variola major virus antigens provide a significant protective immune response when administered as a DNA vaccine that encodes these antigens. Immune responses to variola antigens can be induced by administration of nucleic acids and/or by administration of the variola antigen proteins themselves. Accordingly, in one aspect, the invention features isolated nucleic acid molecules including a first nucleotide sequence encoding a signal peptide, and a second nucleotide sequence encoding a first portion of a vaccinia D8 polypeptide that lacks a transmembrane domain and cytoplasmic tail, wherein the first sequence and the second sequence are linked such that the signal peptide and the portion of the D8 polypeptide are expressed as a fusion polypeptide. In various embodiments, the portion of the D8 antigen comprises a sequence at least 80%, 85%, 90%, 95%, 97%, or 99% identical to SEQ ID NO:4.

The signal peptide can be mammalian, e.g., human. For example, the signal peptide is a human tissue plasminogen activator (tPA) signal peptide. In various embodiments, the signal peptide has the following amino acid sequence: MDAMKRGLCCVLLLCGAVFVSAS (SEQ ID NO:21), or the signal peptide has the sequence of SEQ ID NO:21 with one, two, three, four, five, six, or seven amino acid substitutions or deletions.

In various embodiments, the first nucleotide sequence and second nucleotide sequence together encode a polypeptide having an amino acid sequence at least 80%, 85%, 90%, 95%, 97%, or 99% identical to SEQ ID NO:6.

In some embodiments, the nucleotide sequence encoding the portion of the vaccinia D8 polypeptide is codon optimized for expression in a mammalian cell. In some embodiments, the sequence is also optimized for expression in a bacterial cell (e.g., the sequence includes codons that are favored in both mammalian and bacterial cells).

In another aspect, the invention features compositions including one or more nucleic acid molecules encoding a signal peptide and a portion of a vaccinia D8 polypeptide, and the composition further includes one or more second nucleic acid molecules that include a nucleotide sequence encoding a second poxvirus polypeptide (e.g., a vaccinia virus polypeptide, or a variola virus polypeptide) or antigenic portion thereof (e.g., a second vaccinia polypeptide selected from the group consisting of an A27 polypeptide, a B5 polypeptide, an A33 polypeptide, and an L1 polypeptide).

In various embodiments, the A27 polypeptide has an amino acid sequence at least 80%, 85%, 90%, 95%, 97%, or 99% identical to SEQ ID NO:8; the B5 polypeptide has an amino acid sequence at least 80%, 85%, 90%, 95%, 97%, or 99% identical to SEQ ID NO:10; the L1 polypeptide has an amino acid sequence at least 80%, 85%, 90%, 95%, 97%, or 99% identical to SEQ ID NO:12; and the A33 polypeptide has an amino acid sequence at least 80%, 85%, 90%, 95%, 97%, or 99% identical to SEQ ID NO:14.

The antigenic portion of the vaccinia polypeptide can be at least 20, 30, 40, 50, 60, 70, 80, 90, or 100 amino acids in length.

The compositions can further include a third nucleic acid molecule encoding a third vaccinia polypeptide or antigenic portion thereof. In various embodiments, the second vaccinia polypeptide can be A27 and the third vaccinia polypeptide is B5.

The composition can further include a fourth nucleic acid encoding a fourth vaccinia polypeptide or antigenic portion thereof. For example, the fourth vaccinia polypeptide can be A33 or L1.

In some embodiments, the nucleotide sequence encoding the second, third, or fourth vaccinia polypeptide is codon optimized for expression in a mammalian cell. In some embodiments, the sequence is also optimized for expression in a bacterial cell (e.g., the sequence includes codons that are favored in both mammalian and bacterial cells). The sequence encoding the second, third, or fourth vaccinia polypeptide can further include a sequence encoding a signal peptide (e.g., a mammalian signal peptide, such as a human signal peptide, e.g., a human tPA signal peptide).

The invention also features cells and expression vectors that include nucleic acid molecules encoding a signal peptide and a portion of a vaccinia D8 polypeptide that lacks a transmembrane domain and cytoplasmic tail. The nucleic acid molecules can include other features described herein.

The invention also features methods for producing a modified vaccinia polypeptide by culturing cells including a nucleic acid molecule that includes a first nucleotide sequence encoding a signal peptide, and a second nucleotide sequence encoding a first portion of a vaccinia D8 polypeptide that lacks a transmembrane domain and cytoplasmic tail, under conditions in which the first sequence and second sequence are expressed as a fusion polypeptide, and isolating the expressed fusion polypeptide.

The invention also features compositions including nucleic acid molecules encoding a signal peptide and a portion of a vaccinia D8 polypeptide that lacks a transmembrane domain and cytoplasmic tail, and a pharmaceutically acceptable carrier.

The invention also features methods of inducing an immune response to a poxvirus in a mammal by administering to a mammal a composition including a nucleic acid molecule as described herein in an amount sufficient to produce an immune response in the mammal. The nucleic acid molecule can include a first nucleotide sequence encoding a signal peptide, and a second nucleotide sequence encoding a first portion of a vaccinia D8 polypeptide that lacks a transmembrane domain and cytoplasmic tail, wherein the first sequence and the second sequence are linked such that the signal peptide and the portion of the D8 polypeptide are expressed as a fusion polypeptide The immune response produced by the nucleic acid molecule can be a protective immune response (e.g., a response that protects against a subsequent poxvirus infection).

The mammal can be a non-human mammal or a human (e.g., a human sero-negative for vaccinia or variola, e.g., a human at risk for infection with a poxvirus.).

The composition administered to the mammal can include additional nucleic acid molecules (e.g., it can include a second nucleic acid molecule including a nucleotide sequence encoding a second vaccinia polypeptide or antigenic portion thereof, or a second nucleic acid molecule encoding a variola polypeptide or antigenic portion thereof). In some embodiments, the composition administered to the mammal further includes nucleic acid molecules comprising nucleotide sequences encoding two, three, or all four of the following: an A27 polypeptide or an antigenic portion thereof, a B5 polypeptide or an antigenic portion thereof, an A33 polypeptide or an antigenic portion thereof; and an L1 polypeptide or an antigenic portion thereof.

The methods of administering nucleic acid molecules to mammals can further include administering a composition including a poxvirus polypeptide (e.g., a vaccinia polypeptide or variola peptide, e.g., a recombinant vaccinia polypeptide or variola polypeptide, e.g., a vaccinia polypeptide or variola peptide described herein). The methods can include administering a vaccinia virus composition (e.g., an attenuated vaccinia virus vaccine). The polypeptide or virus composition can be administered simultaneous with, prior to, or after administration of the nucleic acid molecule. The nucleic acid molecule(s) and/or the polypeptide or virus compositions can be administered multiple times (e.g., two, three, four, or five times).

The invention also features novel compositions including variola sequences and modified forms thereof. For example, in one aspect, the invention features isolated nucleic acid molecules including a nucleotide sequence encoding a variola F8 polypeptide or antigenic portion thereof. In some embodiments, the nucleotide sequences are codon optimized for expression in mammalian cells. The sequences can include a nucleotide sequence at least 80%, 85%, 90%, 95%, 97%, or 99% identical to SEQ ID NO:15.

In various embodiments, the codon optimized nucleotide sequences encoding F8, or a portion thereof; are linked to a nucleotide sequence encoding a signal peptide such that the signal peptide and the F8 polypeptide or portion thereof (e.g., a portion lacking a cytoplasmic tail and transmembrane region, e.g., a portion comprising 100, 125, 150, 175, 200, 225, 250, or 275 amino acids of the N-terminal sequence of the F8 polypeptide) are expressed as a fusion polypeptide. The signal peptide can be mammalian, e.g., human. For example, the signal peptide is a human tissue plasminogen activator (tPA) signal peptide. In various embodiments, the signal peptide has the following amino acid sequence: MDAMKRGLCCVLLLCGAVFVSAS (SEQ ID NO:21). In various embodiments, the signal peptide has the sequence of SEQ ID NO:21 with one, two, three, four, live, six, or seven amino acid substitutions or deletions.

In another aspect, the invention features isolated nucleic acid molecules including a nucleotide sequence encoding a variola A30 polypeptide or antigenic portion thereof. In some embodiments, the nucleotide sequence is codon optimized for expression in a mammalian cell, e.g., the sequence includes and a nucleotide sequence at least 80%, 85%, 90%, 95%, 97%, or 99% identical to SEQ ID NO:17.

In still another aspect, the invention features isolated nucleic acid molecules including a nucleotide sequence encoding a variola B7 polypeptide or antigenic portion thereof. In some embodiments, the nucleotide sequence is codon optimized for expression in a mammalian cell, e.g., the sequence a nucleotide sequence at least 80%, 85%, 90%, 95%, 97%, or 99% identical to SEQ ID NO:19. The antigenic portion of the variola polypeptide can be at least 20, 30, 40, 50, 60, 70, 80, 90, or 100 amino acids in length.

In some embodiments, the variola sequences are optimized for expression in bacterial cells (e.g., the sequence includes codons that are favored for expression in both mammalian and bacterial cells).

The invention also features methods of inducing an immune response to a poxvirus in a mammal by administering to a mammal a composition including a nucleic acid molecule, wherein the nucleic acid molecule includes one or more nucleotide sequences, each encoding a variola F8, A30, or B7 polypeptide or antigenic portion thereof. In various embodiments, one or more of the nucleotide sequences are codon optimized for expression in a mammalian cell. The composition is administered in an amount effective to produce an immune response in the mammal, e.g., the composition is administered in an amount sufficient to induce a protective immune response against a subsequent poxvirus infection. The mammal can be a non-human mammal or a human (e.g., a human sero-negative for vaccinia or variola, e.g., a human at risk for infection with a poxvirus).

In various embodiments, at least one of the one or more nucleotide sequences has a sequence at least 80%, 85%, 90%, 95%, 97%, or 99% identical to SEQ ID NO:15, 17, or 19.

In various embodiments, the methods further include administering a nucleic acid molecule encoding a vaccinia polypeptide or antigenic portion thereof. The methods of administering a nucleic acid molecule to a mammal can further include administering a composition including a poxvirus polypeptide (e.g., a vaccinia polypeptide or variola peptide, e.g., a recombinant vaccinia polypeptide or variola polypeptide, e.g., a vaccinia polypeptide or variola peptide described herein). The methods can include administering a vaccinia virus composition (e.g., an attenuated vaccinia virus vaccine). The polypeptide or virus composition can be administered simultaneous with, prior to, or after administration of the nucleic acid molecule. The nucleic acid molecule(s) and/or the polypeptide or virus compositions can be administered multiple times (e.g., two, three, four, or five times Calculations of "homology" or "identity" between two sequences are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). For substantial identity, the length of a reference sequence aligned for comparison purposes is at least 80%, but can be higher, e.g., at least 85%, 90%, 85%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences are accomplished using a mathematical algorithm. In particular, percent homology between two amino acid sequences is determined using the Needleman and Wunsch, 1970, J. Mol. Biol., 48:444-453, algorithm which has been incorporated into the GAP program in the GCG software package, using a Blossum 62 scoring matrix with a gap penalty of 12, a gap extend penalty of 4, and a frameshift gap penalty of 5.

It is understood that the poxvirus antigens and immunogenic fragments thereof may have additional conservative or non-essential amino acid substitutions, which do not have a substantial effect on the polypeptide functions. Whether or not a particular substitution will be tolerated, i.e., will not adversely affect desired biological properties, such as binding activity, can be determined as described in Bowie et al., 1990, Science, 247:1306-1310. A "conservative amino acid substitution" is one in which an amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of a polypeptide, such as a binding agent, e.g., an antibody, without substantially altering a biological activity (e.g., immunogenicity), whereas an "essential" amino acid residue results in such a change.

Vaccines that employ recombinant proteins and/or DNA to elicit immune responses are safer than live attenuated virus vaccines. Live vaccines are often accompanied by undesirable side effects. However, it has been difficult to generate subunit and DNA vaccines that provide protection as potent as that afforded by live virus vaccines. The discovery of modifications that enhance the immunogenicity of poxvirus DNA and polypeptide sequences as described herein allows for safe and effective means of vaccination. DNA vaccines encoding a truncated form of vaccinia D8 are potent immunogens when administered alone and advantageously enhance the protective response when administered with a second poxvirus vaccine composition, such as a polyvalent DNA vaccine.

An "antigenic portion" of a polypeptide is a fragment sufficient to elicit an antigen-specific immune response (i.e., an antigen-specific antibody response, cellular immune response, or both) in a subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is a schematic diagram of two D8L gene inserts. Locations of the hydrophobic transmembrane (TM) domain, tPA leader sequence, and amino acid positions 1, 275, and 305 are indicated.

FIGS. 2A-2C are graphs depicting IgG antibody titers in sera of mice administered the tPA-D8L or wtD8L DNA vaccines as measured by ELISA. Control groups of mice received either the empty DNA vector (vector) or the vaccinia virus WR strain (WR). FIG. 2A depicts titers against recombinant D8 antigen produced from 293T cells. FIG. 2B depicts titers against lysates of Vero cells infected with vaccinia virus WR strain. FIG. 2C depicts titers of neutralizing antibodies for the same groups of mouse sera. Data shown are geometric means of neutralizing antibody titers which are the highest sera dilution that inhibited 50% of virus infection in the neutralization assay.

FIGS. 5A-5F are graphs depicting IgG antibody titers induced by individual D8L or polyvalent pox DNA vaccine formulations against either the individual pox antigens including A27 (FIG. 5A), B5 (FIG. 5B), D8 (FIG. 5C), L1 (FIG. 5D), A33 (FIG. 5E), or Vero cell lysate infected with vaccinia virus (VACV) (FIG. 5F). Data are shown as the geometric means of end titration titers as determined by ELISA for each group (5 mice per group).

FIG. 5G is a graph depicting titers of neutralizing antibody responses against intracellular mature virus (IMV), shown as the geometric means of the highest serum dilutions that inhibited 50% of virus infection in a plaque reduction assay.

FIG. 6 is a table in which partial sequences of selected protective variola major and vaccinia antigens are aligned. The amino acid sequences of proteins encoded by WR and COP strains of vaccinia virus, as well as variola India1967 and Bangladesh1975 are compared. Numbers shown above amino acids indicate amino acid positions. Amino acids that are different between the strains are shown in bold. Amino acids that are identical in all viruses are shown as dots. Contiguous sequences of four or more amino acid residues are identified as SEQ ID NOs:22-49.

FIGS. 7A-7C are graphs depicting recognition of variola major and vaccinia antigens in sera of animals administered variola DNA vaccines as measured by ELISA. Immune reactivity to A30, A27 (FIG. 7A), F8, D8 (FIG. 7B), B7, and B5 (FIG. 7C) antigens are depicted for the same mouse sera from animals immunized with the combination of three DNA vaccines expressing variola major antigens A30, B7, and F8. Each curve is the average of sera assayed from 10 mice that received three immunizations. Each chart shows one pair of ortholog antigens from both variola and vaccinia.

FIG. 10A is a graph depicting IgG titers against A30, B7, or F8 antigens in sera from animals immunized with either a combination of recombinant A30, B7, and F8 proteins (Protein), or a combination of three DNA vaccines expressing A30, B7, and F8 antigens (DNA). Animals in control groups received one immunization with vaccinia (WR). Data are shown as the geometric means of each group (5 per group) after two immunizations.

FIG. 10B is a graph depicting percent survival in mice that received three immunizations of either the combination of three recombinant variola proteins (rA30, rB7, and rF8) or the combination of three DNA vaccines expressing A30, B7, and F8 prior to lethal intranasal challenge with VACV (WR). Animals in the positive control group received one vaccinia (WR) immunization and animals in the negative control group received three immunizations with an empty DNA vaccine vector. Each curve shows the daily percentage of survivals for each group (five mice per group) after challenge.

Like reference symbols in the various drawings indicate like elements.

DETAILED DESCRIPTION

Figure 3A:
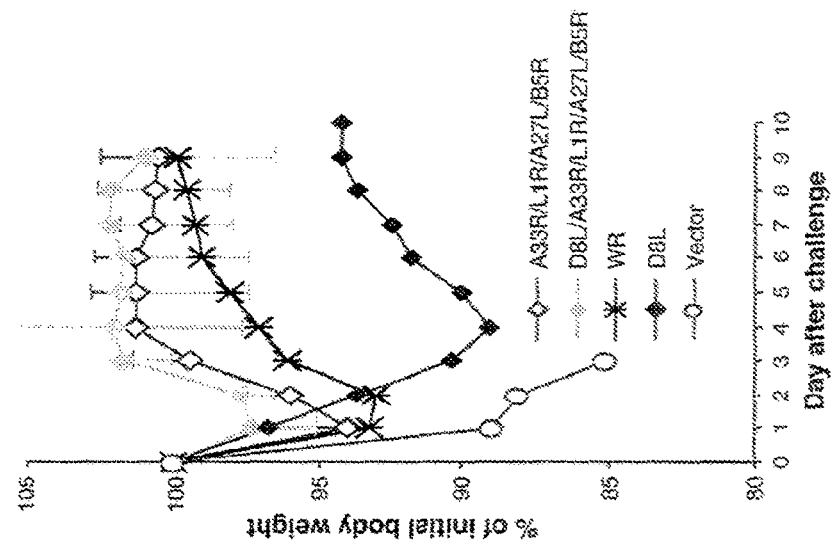
FIGS. 3A-3C are graphs depicting body weight loss as the percentage of pre-challenge weight in mice challenged with vaccinia virus WR strain by the intraperitoneal route. Prior to challenge, mice were administered individual D8L vaccines (wtD8L, tPAD8L) (FIG. 3A), a bivalent pox DNA vaccine formulation (A27L and B5R) with or without a third component (tPA-D8L) (FIG. 3B), or a 4-valent formulation (A27L, B5R, L1R, and A33R) with or without the addition of a fifth component (tPA-D8L). Mice in the positive control group were immunized with $10^5$ pfu of vaccinia virus WR strain 2 weeks prior to challenge (WR). Mice in the negative control group (vector) received empty DNA vector. Each curve shows the group average weight loss (10 mice per group).
Figure 3B:
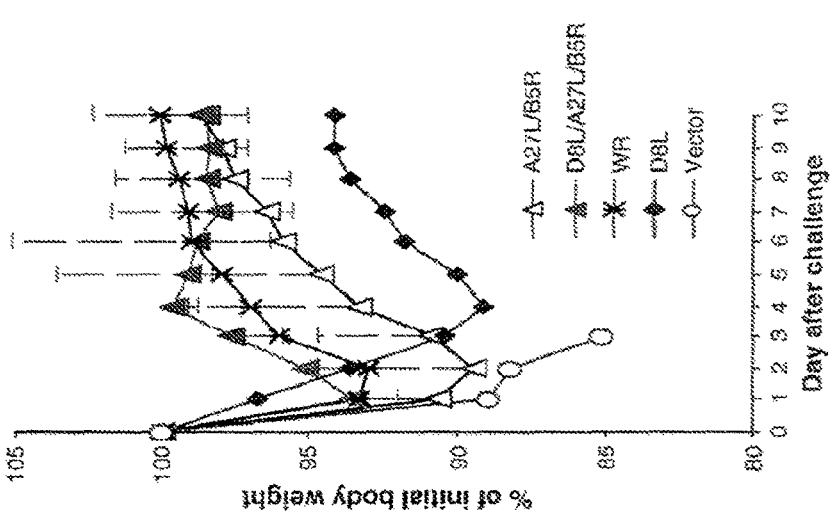
Figure 3C:
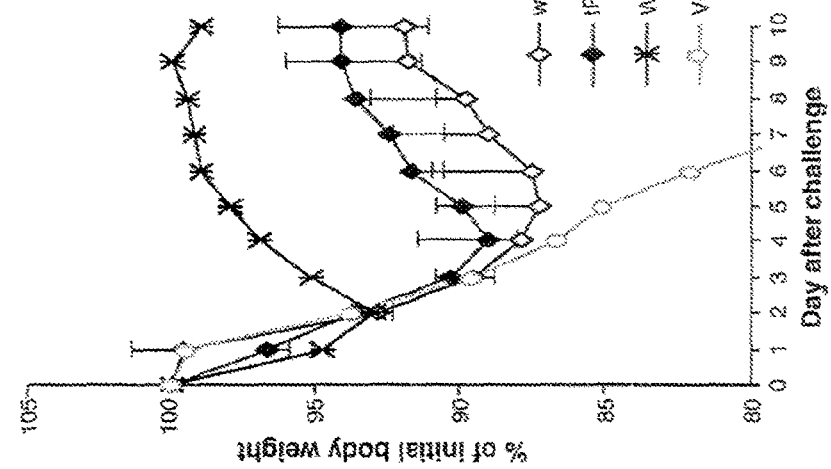

Side effects associated with live, attenuated vaccinia virus vaccines have prompted the need for safer means of immunizing against smallpox, but it has been a great challenge to develop DNA or protein subunit vaccines for immunization that have a protective efficacy comparable to that achieved with standard, live virus vaccines. The compositions described herein provide novel forms of poxvirus antigens, including variola major and vaccinia virus antigens, combinations of antigens, and nucleic acid sequences encoding the antigens that avoid the problems of live virus vaccines, yet unexpectedly provide potent protection against infection.

One of the poxvirus antigens is D8 (SEQ ID NO:2 in Table 1, below), encoded by the D8L gene (SEQ ID NO:1 in Table 1, below). D8 is an envelope protein of the IMV form of vaccinia. D8 mediates adsorption of IMV to cells (Maa et al., 1990, J. Biol. Chem., 265(3): 1569-1577). The new methods and compositions are based, at least in part, on the finding that truncation of D8 to remove its transmembrane domain and cytoplasmic tail significantly enhances its immunogenicity. One such modified form is encoded by the tPA-D8L DNA construct described herein, which expresses a truncated form of D8 as a fusion with an N-terminal human tissue plasminogen activator (tPA) leader sequence. The tPA-D8L DNA sequence (SEQ ID NO:5) and amino acid sequence (SEQ ID NO:6) are shown in Table 1, below.

It has been discovered that immunization with DNA encoding D8, or a modified form of D8, induces neutralizing antibody responses and provides protection from subsequent lethal virus challenge (i.e., it provides a protective immune response). Furthermore, the addition of DNA encoding a modified D8 antigen to polyvalent DNA vaccines significantly improves their protective efficacy. Accordingly, D8L and modified forms (e.g., truncated forms, forms expressed with a heterologous signal sequence) of D8L can be used with DNA encoding one or more additional poxvirus antigens, such as A27L, B5R, L1R, or A33R of vaccinia, or A30L, B7R, or F8L of variola major. Polypeptide compositions that include these antigens are also useful for inducing immunity to poxviruses.

Also provided herein are methods and compositions including A30, B7, and F8 antigens of variola major and nucleic acid molecules encoding these antigens. For example, modified A30L, B7R, and F8L genes that are codon optimized for expression in mammalian (e.g., human) cells are provided. A30, B7, and F8 are highly homologous to A27, B5, and D8 proteins of vaccinia, respectively. Immunization with variola DNA or protein antigen compositions provide cross-protection against subsequent infections by the homologous vaccinia antigen, and vice versa.

Herein, the genes encoding vaccinia D8, A27, B5, L1, and A33 proteins are called D8L, A27L, B5R, L1R, and A33R, respectively. The genes encoding variola A30, B7, and F8 proteins are called A30L, B7R, and F8L, respectively. The sequences are all shown in Table 1 below.

Modified Poxvirus Antigens

The expression and/or immunogenicity of poxvirus DNA vaccines and poxvirus antigens can be enhanced by modifying native poxvirus gene sequences. One type of modification that facilitates expression is to express the antigen with a heterologous signal peptide, also referred to herein as a signal sequence. The signal sequence may be cleaved from the poxvirus antigen during or after synthesis of the polypeptide. A signal sequence is a peptide that directs a polypeptide into the secretory pathway during synthesis in the cell. Signal sequences are typically located at the extreme N-terminus of a polypeptide, and can be clipped off by enzymes within the host cell prior to the final steps of trafficking and secretion. Signal sequences typically have an N-terminal region of approximately 2-15 amino acids, which has a net positive charge, followed by a hydrophobic region of 8 amino acids or more, and a neutral, but polar, C-terminal region. Residues at positions 23 and 21, relative to the signal peptidase cleavage site, must be small and neutral for cleavage to occur correctly (von Heijne, 1983, Eur. J. Biochem., 133:17-21; von Heijne, 1985, J. Mol. Biol., 184: 99-105). Numerous signal sequences are known to those of skill in the art. The use of any of these signal sequences is contemplated and those described herein are not limiting. Certain signal sequences can be found associated with a variety of proteins native to prokaryotes and eukaryotes, such as tissue plasminogen activator (tPA) signal sequence, alpha factor leader sequence, and the like. "Leader sequence, signal sequence, and signal peptide" are used interchangeably herein.

In certain embodiments, the signal sequence is a mammalian (e.g., human) signal sequence. For example, the sequence can be a tissue plasminogen activator signal sequence or a signal sequence that has the same function as a tPA signal sequence. An exemplary tPA signal sequence has the following amino acid sequence:

MDAMKRGLCCVLLLCGAVFVSAS. (SEQ ID NO: 21)

Another type of modification involves deletion of a region of the native poxvirus gene sequence. In various embodiments, regions of a poxvirus gene sequence are deleted to construct a modified antigen. For example, D8L constructs are generated in which a hydrophobic (e.g., transmembrane) region is deleted. The transmembrane region of D8 is located at amino acids 275-294 of SEQ ID NO:2 (see Table 1, below). In some embodiments, the cytosolic tail of D8 is deleted. The cytosolic tail of D8 is located at amino acids 295-304 of SEQ ID NO:2. Sequences modified in this manner can be more efficiently expressed in cells. In some cases, truncated antigens are differentially glycosylated as well. It was discovered that the truncated D8 polypeptide encoded by the tPA-D8L construct is glycosylated, whereas D8 expressed by vaccinia virus is primarily non-glycosylated.

Another type of modification of poxvirus antigens is codon optimization. Viral proteins and proteins that are naturally expressed at low levels can provide challenges for efficient expression by recombinant means. Viral proteins often display a codon usage that is inefficiently translated in a host cell. Alteration of the native viral codons can facilitate more robust expression of these proteins. Codon preferences for abundantly-expressed proteins have been determined in a number of species, and can provide guidelines for codon substitution. Examples of human proteins for which codon preferences have been determined include rhodopsin. Substitution of viral codons can be done by known methods, such as site-directed mutagenesis, or construction of oligonucleotides corresponding to the optimized sequence and synthesis of sequences by PCR. See, e.g., the construction method described in Mirzabekov T. et al., 1999, J. Biol. Chem., 274(40):28745-50. The optimization should also include consideration of other factors that can affect synthesis of oligos and/or expression. For example, long runs of G and/or C residues can interfere with synthesis, and should be avoided in the resulting optimized sequence.

We have surprisingly found that certain codon optimized sequences can be successfully expressed in both mammalian and bacterial cells. Codon optimization for both mammalian and bacterial (e.g., E. coli) expression is performed as follows. Some codons that are most preferred for mammalian expression (i.e., most efficiently translated in mammalian cells) are also most preferred for bacterial expression. Substitution of viral codons for these most preferred codons allows optimization for expression in both systems. However, some codons that are most preferred for mammalian expression are not most preferred for bacterial expression. For these codons, both mammalian and E. coli preferred codons and codons expressed with intermediate efficiency in both types of cells may be used to substitute for the viral codon. In addition, during the sequence optimization, following cis-acting sequence motifs are avoided: internal TATA-boxes, chi-sites and ribosomal entry sites; AT-rich or GC-rich sequence stretches; ARE, INS, CRS sequence elements; cryptic splice donor and acceptor sites; and branch points. Codon optimized sequences can retain some of the original codons. For example, a codon optimized sequence retains less than 70%, 60%, 50%, 40%, 30%, 20%, or 10% of the original viral codons.

Exemplary codon optimized variola sequences are shown in Table 1 (below).

TABLE 1

Poxvirus Antigen Sequences

| Gene/protein name | Sequence |
|---|---|
| D8L | atgccgcaacaactatctcctattaatatagaaactaaaaaagcaatttctaacg<br>cgcgattgaagccgttagacatacattataatgagtcgaaaccaaccactatcca<br>gaacactggaaaactagtaaggattaattttaaaggaggatatataagtggaggg<br>tttctccccaatgaatatgtgttatcatcactacatatatattggggaaaggaag<br>acgattatggatccaatcacttgatagatgtgtacaaatactctggagagattaa<br>tcttgttcattggaataagaaaaaatatagttcttatgaagaggcaaaaaaacac<br>gatgatggacttatcattatttctatattcttacaagtattggatcataaaaatg |

TABLE 1-continued

Poxvirus Antigen Sequences

| Gene/protein name | Sequence |
|---|---|
| | tatattttcaaaagatagttaatcaattggattccattagatccgccaatacgtc<br>tgcaccgtttgattcagtattttatctagacaatttgctgcctagtaagttggat<br>tattttacatatctaggaacaactatcaaccactctgcagacgctgtatggataa<br>ttttccaacgccaataaacattcattctgatcaactatctaaattcagaacact<br>attgtcgtcgtctaatcatgatggaaaaccgcattatataacagagaactataga<br>aatccgtataaattgaacgacgacacgcaagtatattattctggggagattatac<br>gagcagcaactacctctccagcgcgcgagaactattttatgagatggttgtccga<br>tttgagagagacatgttttcatattatcaaaaatatatcgaagagaataaaaca<br>ttcgcaattattgccatagtattcgtgtttatacttaccgctattctcttttta<br>tgagtcgacgatattcgcgagaaaaacaaaactag<br>(SEQ ID NO: 1) |
| D8 | MPQQLSPINIETKKAISNARLKPLDIHYNESKPTTIQNTGKLVRINFKGGYISGG<br>FLPNEYVLSSLHIYWGKEDDYGSNHLIDVYKYSGEINLVHWNKKKYSSYEEAKKH<br>DDGLIIISIFLQVLDHKNVYFQKIVNQLDSIRSANTSAPFDSVFYLDNLLPSKLD<br>YFTYLGTTINHSADAVWIIFPTPINIHSDQLSKFRTLLSSSNHDGKPHYITENYR<br>NPYKLNDDTQVYYSGEIIRAATTSPARENYFMRWLSDLRETCFSYYQKYIEENKT<br>FAIIAIVFVFILTAILFFMSRRYSREKQN<br>(SEQ ID NO: 2) |
| D8L$_{(1-275)}$ | atgccgcaacaactatctcctattaatatagaaactaaaaaagcaatttctaacg<br>cgcgattgaagccgttagacatacattataatgagtcgaaaccaaccactatcca<br>gaacactggaaaactagtaaggattaattttaaaggaggatatataagtggaggg<br>tttctccccaatgaatatgtgttatcatcactacatatatattgggggaaaggaag<br>acgattatggatccaatcacttgatagatgtgtacaaatactctggagagattaa<br>tcttgttcattggaataagaaaaaatatagttcttatgaagaggcaaaaaaacac<br>gatgatggacttatcattatttctatattcttacaagtattggatcataaaaatg<br>tatattttcaaaagatagttaatcaattggattccattagatccgccaatacgtc<br>tgcaccgtttgattcagtattttatctagacaatttgctgcctagtaagttggat<br>tattttacatatctaggaacaactatcaaccactctgcagacgctgtatggataa<br>ttttccaacgccaataaacattcattctgatcaactatctaaattcagaacact<br>attgtcgtcgtctaatcatgatggaaaaccgcattatataacagagaactataga<br>aatccgtataaattgaacgacgacacgcaagtatattattctggggagattatac<br>gagcagcaactacctctccagcgcgcgagaactattttatgagatggttgtccga<br>tttgagagagacatgttttcatattatcaaaaatatatcgaagagaataaaaca<br>(SEQ ID NO: 3) |
| D8$_{(1-275)}$ | MPQQLSPINIETKKAISNARLKPLDIHYNESKPTTIQNTGKLVRINFKGGYISGG<br>FLPNEYVLSSLHIYWGKEDDYGSNHLIDVYKYSGEINLVHWNKKKYSSYEEAKKH<br>DDGLIIISIFLQVLDHKNVYFQKIVNQLDSIRSANTSAPFDSVFYLDNLLPSKLD<br>YFTYLGTTINHSADAVWIIFPTPINIHSDQLSKFRTLLSSSNHDGKPHYITENYR<br>NPYKLNDDTQVYYSGEIIRAATTSPARENYFMRWLSDLRETCFSYYQKYIEENKT<br>(SEQ ID NO: 4) |
| tPA-D8L | ATGGATGCAATGAAGAGAGGGCTCTGCTGTGTGCTGCTGCTGTGTGGAGCAGTCT<br>TCGTTTCGGCTAGCCCGCAACAACTATCTCCTATTAATATAGAAACTAAAAAAGC<br>AATTTCTAACGCGCGATTGAAGCCGTTAGACATACATTATAATGAGTCGAAACCA<br>ACCACTATCCAGAACACTGGAAAACTAGTAAGGATTAATTTTAAAGGAGGATATA<br>TAAGTGGAGGGTTCTCCCCCAATGAATATGTGTTATCATCACTACATATATATTG<br>GGGAAAGGAAGACGATTATGGATCCAATCACTTGATAGATGTGTACAAATACTCT<br>GGAGAGATTAATCTTGTTCATTGGAATAAGAAAAAATATAGTTCTTATGAAGAGG<br>CAAAAAAACACGATGATGGACTTATCATTATTTCTATATTCTTACAAGTATTGGA<br>TCATAAAAATGTATATTTTCAAAAGATAGTTAATCAATTGGATTCCATTAGATCC<br>GCCAATACGTCTGCACCGTTTGATTCAGTATTTTATCTAGACAATTTGCTGCCTA<br>GTAAGTTGGATTATTTTACATATCTAGGAACAACTATCAACCACTCTGCAGACGC<br>TGTATGGATAATTTTTCCAACGCCAATAAACATTCATTCTGATCAACTATCTAAA<br>TTCAGAACACTATTGTCGTCGTCTAATCATGATGGAAAACCGCATTATATAACAG<br>AGAACTATAGAAATCCGTATAAATTGAACGACGACACGCAAGTATATTATTCTGG<br>GGAGATTATACGAGCAGCAACTACCTCTCCAGCGCGCGAGAACTATTTTATGAGA<br>TGGTTGTCCGATTTGAGAGAGACATGTTTTTCATATTATCAAAAATATATCGAAG<br>AGAATAAACATTCGCATAG<br>(SEQ ID NO: 5) |
| tPA-D8 | MDAMKRGLCCVLLLCGAVFVSASPQQLSPINIETKKAISNARLKPLDIHYNESKP<br>TTIQNTGKLVRINFKGGYISGGFLPNEYVLSSLHIYWGKEDDYGSNHLIDVYKYS<br>GEINLVHWNKKKYSSYEEAKKHDDGLIIISIFLQVLDHKNVYFQKIVNQLDSIRS<br>ANTSAPFDSVFYLDNLLPSKLDYFTYLGTTINHSADAVWIIFPTPINIHSDQLSK<br>FRTLLSSSNHDGKPHYITENYRNPYKLNDDTQVYYSGEIIRAATTSPARENYFMR<br>WLSDLRETCFSYYQKYIEENKTFA<br>(SEQ ID NO: 6) |
| A27L | atggacggaactcttttcccccggagatgacgatcttgcaattccagcaactgaat<br>ttttttctacaaaggctgctaaaaagccagaggctaaacgcgaagcaattgttaa<br>agccgatgaagacgacaatgaggaaactctcaaacaacggctaactaatttggaa |

TABLE 1-continued

Poxvirus Antigen Sequences

| Gene/protein name | Sequence |
|---|---|
| | aaaaagattactaatgtaacaacaaagtttgaacaaatagaaaagtgttgtaaac<br>gcaacgatgaagttctatttaggttggaaaatcacgctgaaactctaagagcggc<br>tatgatatctctggctaaaaagattgatgttcagactggacggcgcccatgag<br>taa<br>(SEQ ID NO: 7) |
| A27 | MDGTLFPGDDDLAIPATEFFSTKAAKKPEAKREAIVKADEDDNEETLKQRLTNLE<br>KKITNVTTKFEQIEKCCKRNDEVLFRLENHAETLRAAMISLAKKIDVQTGRRPYE<br>(SEQ ID NO: 8) |
| B5R | atgaaaacgatttccgttgttacgttgttatgcgtactacctgctgttgtttatt<br>caacatgtactgtacccactatgaataacgctaaattaacgtctaccgaaacatc<br>gtttaatgataaacagaaagttacgtttacatgtgatcagggatatcattcttcg<br>gatccaaatgctgtctgcgaaacagataaatggaaatacgaaatccatgcaaaa<br>aaatgtgcacagtttctgattacatctctgaattatataataaaccgctatacga<br>agtgaattccaccatgacactaagttgcaacggcgaaacaaaatattttcgttgc<br>gaagaaaaaaatggaaatacttcttggaatgatactgttacgtgtcctaatgcgg<br>aatgtcaacctcttcaattagaacacggatcgtgtcaaccagttaaagaaaaata<br>ctcatttggggaatatatgactatcaactgtgatgttggatatgaggttattggt<br>gcttcgtacataagttgtacagctaattcttggaatgttattccatcatgtcaac<br>aaaaaatgtgatatgccgtctctatctaatggattaatttccggatctacattttc<br>tatcggtggcgttatacatcttagttgtaaaagtggttttacactaacggggtct<br>ccatcatccacatgtatcgacggtaaatggaatcccgtactcccaatatgtgtac<br>gaactaacgaagaatttgatccagtggatgatggtcccgaactgatgagacagatt<br>gagcaaactctcgaaagacgttgtacaatatgaacaagaaatagaatcgttagaa<br>gcaacttatcatataatcatagtggcgttaacaattatgggcgtcatattttaa<br>tctccgttatagtattagtttgttcctgtgacaaaaataatgaccaatataagtt<br>ccataaattgctaccgtaa<br>(SEQ ID NO: 9) |
| B5 | MKTISVVTLLCVLPAVVYSTCTVPTMNNAKLTSTETSFNDKQKVTFTCDQGYHSS<br>DPNAVCETDKWKYENPCKKMCTVSDYISELYNKPLYEVNSTMTLSCNGETKYFRC<br>EEKNGNTSWNDTVTCPNAECQPLQLEHGSCQPVKEKYSFGEYMTINCDVGYEVIG<br>ASYISCTANSWNVIPSCQQKCDMPSLSNGLISGSTFSIGGVIHLSCKSGFTLTGS<br>PSSTCIDGKWNPVLPICVRTNEEFDPVDDGPDDETDLSKLSKDVVQYEQEIESLE<br>ATYHIIVALTIMGVIFLISVIVLVCSCDKNNDQYKFHKLLP<br>(SEQ ID NO: 10) |
| L1R | atgggtgccgcggcaagcatacagacgacggtgaatacactcagcgaacgtatct<br>cgtctaaattagaacaagaagcgaatgctagtgctcaaacaaaatgtgatataga<br>aatcggaaattttatatccgacaaaaccatggatgtaacctcactgttaaaaat<br>atgtgctctgcggacgcggatgctcagttggatgctgtgttatcagccgctacag<br>aaacatatagtggattaacaccggaacaaaaagcatacgtgccagctatgtttac<br>tgctgcgttaaacattcagacgagtgtaaacactgttgttagagattttgaaaat<br>tatgtgaaacagacttgtaattctagccgcggtcgtcgataacaaattaaagatac<br>aaaacgtaatcatagatgaatgttacggagccccaggatctccaacaaatttgga<br>atttattaatacaggatctagcaaaggaaattgtgccattaaggcgttgatgcaa<br>ttgacgactaaggccactactcaaatagcacctaaacaagttgctggtacaggag<br>ttcagtttatatgattgttatcggtgttataatattggcagcgttgtttatgta<br>ctatgccaagcgtatgttgttcacatccaccaatgataaaatcaaacttatttta<br>gccaataaggaaaacgtccattggactacttacatggacacattctttagaactt<br>ctccgatggttattgctaccacgatatgcaaaactga<br>(SEQ ID NO: 11) |
| L1 | MGAAASIQTTVNTLSERISSKLEQEANASAQTKCDIEIGNFYIRQNHGCNLTVKN<br>MCSADADAQLDAVLSAATETYSGLTPEQKAYVPAMFTAALNIQTSVNTVVRDFEN<br>YVKQTCNSSAVVDNKLKIQNVIIDECYGAPGSPTNLEFINTGSSKGNCAIKALMQ<br>LTTKATTQIAPKQVAGTGVQFYMIVIGVIILAALFMYYAKRMLFTSTNDKIKLIL<br>ANKENVHWTTYMDTFFRTSPMVIATTDMQN<br>(SEQ ID NO: 12) |
| A33R | atgatgacaccagaaaacgacgaagagcagacatctgtgttctccgctactgttt<br>acggagacaaaattcaaggaaagaataaacgcaaacgcgtgattggtctatgtat<br>tagaatatctatggttatttcactactatctatgattaccatgtccgcgtttctc<br>atagtgcgcctaaatcaatgcatgtctgctaacgaggctgctattactgacgccg<br>ctgttgccgttgctgctgcatcatctactcatagaaaggttgcgtctagcactac<br>acaatatgatcacaaagaaagctgtaatggtttatattaccagggttcttgttat<br>atattacattcagactaccagttattctcggatgctaaagcaaattgcactgcgg<br>aatcatcaacactacccaataaatccgatgtcttgattacctggctcattgatta<br>tgttgaggatacatgggatctgatggtaatccaattacaaaaaactacatccgat<br>tatcaagattctgatgtatcacaagaagttagaaagtatttttgtgttaaaacaa<br>tgaactaa<br>(SEQ ID NO: 13) |

TABLE 1-continued

Poxvirus Antigen Sequences

| Gene/protein name | Sequence |
|---|---|
| A33 | MMTPENDEEQTSVFSATVYGDKIQGKNKRKRVIGLCIRISMVISLLSMITMSAFL<br>IVRLNQCMSANEAAITDAAVAVAAASSTHRKVASSTTQYDHKESCNGLYYQGSCY<br>ILHSDYQLFSDAKANCTAESSTLPNKSDVLITWLIDYVEDTWGSDGNPITKTTSD<br>YQDSDVSQEVRKYFCVKTMN<br>(SEQ ID NO: 14) |
| codon optimized F8L | CTGCAGGCTAGCATGAGCCAGCAACTGAGCCCCATCAACATCGAGACCAAGAAGG<br>CCATCAGCAACGCACGCCTGAAGCCCCTGAACATCCACTACAACGAGAGCAAGCC<br>CACCACCATCCAGAACACCGGCAAGCTGGTGCGCATCAACTTCAAGGGAGGCTAC<br>CTGAGCGGAGGCTTCCTTCCCAACGAGTACGTGCTGAGCAGCCTGCACATCTACT<br>GGGGCAAGGAGGATGACTACGGCAGCAACCACCTGATCGACGTGTACAAGTACAG<br>CGGCGAGATCAACCTGGTGCACTGGAACAAGAAGTACAGCAGCTACGAGGAA<br>GCCAAGAAGCACGACGATGGCCTGATCATCATCAGCATCTTCCTTCAGGTGAGCG<br>ACCACAAGAACGTGTACTTCCAGAAGATCGTGAACCAACTGGACAGCATCCGCAC<br>TGCCAACACCAGCGCTCCCTTCGACAGCGTGTTCTACCTGGACAACCTGCTGCCC<br>AGCAAGCTGGACTACTTCAAGTACCTAGGCACCACCATCAACCACAGTGCCGACG<br>CCGTGTGGATCATCTTTCCCACCCCTATCAACATCCACAGCGACCAACTGAGCAA<br>GTTCCGCACCCTGCTGAGCCTGAGCAACCATGAGGGCAAGCCCCACTACATCACC<br>GAGAACTACCGCAATCCCTACAAGCTGAACGACGATACCGAGGTGTACTACAGTG<br>GCGAGATCATCCGAGCCGCCACCACCAGCCCTGCTCGCGAGAACTACTTCATGCG<br>CTGGCTGAGCGACCTGCGCGAGACCTGCTTCAGCTACTACCAGAAGTACATCGAG<br>GGCAACAAGACCTTCGCCATCATCGCCATCGTGTTCGTGTACATCCTGACCGCCA<br>TCCTGTTCCTGATGAGCCGCCGATACAGCCGCGAGAAGCAGAACTAAGGATCC<br>(SEQ ID NO: 15) |
| F8 | MSQQLSPINIETKKAISNARLKPLNIHYNESKPTTIQNTGKLVRINFKGGYLSGGFLPNEY<br>VLSSLHIYWGKEDDYGSNHLIDVYKYSGEINLVHWNKKYSSYEEAKKHDDGLIIISIFLQ<br>VSDHKNVYFQKIVNQLDSIRTANTSAPFDSVFYLDNLLPSKLDYFKYLGTTINHSADAVWI<br>IFPTPINIHSDQLSKFRTLLSLSNHEGKPHYITENYRNPYKLNDDTEVYYSGEIIRAATTS<br>PARENYFMRWLSDLRETCFSYYQKYIEGNKTFAIIAIVFVYILTAILFLMSRRYSREKQN<br>(SEQ ID NO: 16) |
| codon optimized A30L | CTGCAGGCTAGCATGGACGGCACCCTGTTCCCTGGCGACGACGACCTGGCCATCC<br>CCGCCACCGAGTTCTTCAGCACCAAGGCTGCCAAGAAGCCTGAGGCCAAGCGCGA<br>GGCCATCGTGAAGGCTGACGGCGACAACAACGAGGAGACCCTGAAGCAGCGCCTG<br>ACCAACCTGGAGAAGAAGATCACCAACGTGACCACCAAGTTCGAGCAGATCGAGA<br>AGTGCTGCAAGCGCAACGACGACGTGCTGTTCCGCCTGGAGAACCACGCCGAGAC<br>CCTGCGCGCTGCCATGATCAGCCTGGCCAAGAAGATCGACGTGCAGACTGGCAGA<br>CGCCCCTACGAGTAAGGATCC<br>(SEQ ID NO: 17) |
| A30 | MDGTLFPGDDDLAIPATEFFSTKAAKKPEAKREAIVKADGDNNEETLKQRLTNLE<br>KKITNVTTKFEQIEKCCKRNDDVLFRLENHAETLRAAMISLAKKIDVQTGRRPYE<br>(SEQ ID NO: 18) |
| codon optimized B7R | CTGCAGATGAAGACCATCAGCGTGGTGACCCTGCTGTGCGTGCTTCCTGCCGTGG<br>TGTACAGCACCTGCACCGTGCCCACCATGAACAACGCCAAGCTGACCAGCACCGA<br>GACCAGCTTCAACGACAAGCAGAAAGTGACCTTCACCTGCGACAGCGGCTACTAC<br>AGCCTGGACCCCAACGCTGTGTGCGAGACCGACAAGTGGAAGTACGAGAATCCCT<br>GCAAGAAGATGTGCACCGTGAGCGACTACGTGAGCGAGCTGTACAACAAACCCCT<br>GTACGAGGTGAACGCTATCATCACCCTGATCTGCAAGGACGAGACCAAGTACTTC<br>CGCTGCGAGGAGAAGAATGGCAACACCAGCTGGAACGACACCGTGACCTGCCCCA<br>ACGCTGAGTGCCAGAGCCTCCAGCTGGACCACGGCAGCTGCCAGCCCGTGAAGGA<br>GAAGTACAGCTTCGGCGAGCACATCACCATCAACTGCGACGTGGGCTACGAGGTG<br>ATCGGTGCCAGCTACATCACCTGCACCGCTAACAGCTGGAACGTGATCCCCAGCT<br>GCCAGCAGAAGTGCGACATTCCCAGCCTGAGCAACGGCCTGATCAGTGGCAGCAC<br>CTTCAGCATCGGTGGCGTGATCCACCTGAGCTGCAAGAGCGGCTTCATCCTGACT<br>GGCAGTCCCAGCAGCACCTGCATCGACGGCAAGTGGAACCCTGTGCTTCCCATCT<br>GCATCCGCAGCAACGAGGAGTTCGACCCCGTGGAGGACGGTCCCGACGACGAGAC<br>CGACCTGAGCAAGCTGAGCAAAGACGTGGTGCAGTACGAGCAGGAGATCGAGAGC<br>CTTGAGGCTACCTACCACATCATTATCGTGGCTCTGACCATCATGGGCGTGATCT<br>TCCTGATCAGCGTGATCGTGCTGGTGTGCAGCTGCAACAAGAACAACGACCAGTA<br>CAAGTTCCACAAGCTGCTTCTGTAAGGATCC<br>(SEQ ID NO: 19) |
| B7 | MKTISVVTLLCVLPAVVYSTCTVPTMNNAKLTSTETSFNDKQKVTFTCDSGYYSL<br>DPNAVCETDKWKYENPCKKMCTVSDYVSELYNKPLYEVNAIITLICKDETKYFRC<br>EEKNGNTSWNDTVTCPNAECQSLQLDHGSCQPVKEKYSFGEHITINCDVGYEVIG<br>ASYITCTANSWNVIPSCQQKCDIPSLSNGLISGSTFSIGGVIHLSCKSGFILTGS<br>PSSTCIDGKWNPVLPICIRSNEEFDPVEDGPDDETDLSKLSKDVVQYEQEIESLE<br>ATYHIIIVALTIMGVIFLISVIVLVCSCNKNNDQYKFHKLLL<br>(SEQ ID NO: 20) |

Nucleic Acid Compositions

The new compositions described herein include nucleic acid compositions that encode poxvirus antigens (e.g., vaccinia antigens and variola antigens). There are many ways of presenting nucleic acid encoding antigen to a host. For example, DNA vaccines can include a naked DNA plasmid that encodes one or more virus antigens. Bacterial vectors (e.g., *Listeria* vectors, Bacille Calmette-Guérin (BCG) vectors), replicon vectors, live attenuated bacteria, DNA vaccine co-delivery with live attenuated vectors, and viral vectors for expression of heterologous genes also can be used. In the case of naked DNA replicon vectors, a mammalian expression plasmid serves as a vehicle for the initial transcription of the replicon. The replicon is amplified within the cytoplasm, resulting in more abundant mRNA encoding the heterologous gene such that initial transfection efficiency may be less important for immunogenicity. In some embodiments, a poxvirus antigen is expressed using a live attenuated viral vector (e.g., recombinant vaccinia (e.g., modified vaccinia Ankara (MVA), IDT Germany), recombinant adenovirus, avian poxvirus (e.g., canarypox (e.g., ALVAC®, Aventis Pasteur) or fowlpox), poliovirus, and alphavirus virion vectors). The avian poxviruses are defective in mammalian hosts, but can express inserted heterologous genes under early promoters. Recombinant adenovirus and poliovirus vectors can thrive in the gut and stimulate efficient mucosal immune responses.

Nucleic acid uptake can be improved in various ways. For example, DNA uptake via intramuscular (IM) delivery of the vaccine can be improved by the addition of sodium phosphate to the formulation. Increased DNA uptake via IM delivery can also be accomplished by electrotransfer (e.g., applying a series of electrical impulses to muscle immediately after DNA immunization). Adjuvants that can also be added to the vaccine (e.g., to improve DNA stability and uptake and/or immune induction) include water emulsions (e.g., complete and incomplete Freund's adjuvant), oil, *Corynebacterium parvum*, BCG, QS-21, iron oxide, sodium alginate, aluminum hydroxide, aluminum and calcium salts (i.e., alum), unmethylated CpG motifs, glucan, and dextran sulfate. Synthetic polymers (e.g., polyamino acids, co-polymers of amino acids, saponin, paraffin oil, muramyl dipeptide, Regressin™ (Vetrepharm, Athens Ga.), and Avridine), and liposomal formulations. These adjuvants can be added to vaccine formulations to improve DNA stability and DNA uptake by the host cells, and may decrease the dosage required to induce an effective immune response. Coinjection of cytokines, ubiquitin, or costimulatory molecules can also help improve immune induction, The antigens described herein can also be fused with cytokine genes, helper epitopes, ubiquitin, or signal sequences to enhance an immune response. Fusions can also be used to aid in targeting to certain cell types.

The medium in which the DNA vector is introduced should be physiologically acceptable for safety reasons. Suitable pharmaceutical carriers include sterile water, Tris-EDTA (TE) buffer, saline, dextrose, glucose, phosphate buffered saline (PBS), or other buffered solutions. Included in the medium can be physiologically acceptable preservatives, stabilizers, diluents, emulsifying agents, pH buffering agents, viscosity enhancing agents, colors, etc.

Once the DNA vaccine is delivered, the nucleic acid molecules (e.g., DNA plasmids; are taken up into host cells, which then express the plasmid DNA as protein. Once expressed, the protein is processed and presented in the context of self-major histocompatibility (MHC) class I and class II molecules. The host then develops an immune response against the DNA-encoded immunogen. To improve the effectiveness of the vaccine, multiple injections can be used for therapy or prophylaxis over extended periods of time. To improve immune induction, a prime-boost strategy can he employed. Priming vaccination with DNA and a different modality for boosting (e.g., live viral vector or protein antigen) has been successful in inducing cell-mediated immunity. The timing between priming and boosting varies and is adjusted for each vaccine.

Nucleic acid vaccines can be administered by many modes and routes. For example, they can be administered intradermally (ID), intramuscularly (IM), and by either route, they can be administered by needle injection, gene gun (e.g., Helios® Gene Gun, Bio-Rad), or needle-less jet injection (e.g., Biojector™ (Bioject Inc., Portland, Oreg.). Other modes of administration include oral, intravenous, intraperitoneal, intrapulmonary, intravitreal, and subcutaneous inoculation. Topical inoculation is also possible, and can be referred to as mucosal vaccination. These include intranasal, ocular, oral, vaginal, or rectal topical routes. Delivery by these topical routes can be by nose drops, eye drops, inhalants, suppositories, or microspheres.

Suitable doses of nucleic acid compositions for humans can range from 1 μg/kg to 1 mg/kg of total nucleic acid, e.g., from 5 μg/kg-500 mg/kg of total DNA, 10 μg/kg-250 μg/kg of total DNA, or 10 μg/kg -170 μg/kg of total DNA. In one embodiment, a human subject (18-50 years of age, 45-75 kg) is administered 1.2 mg-7.2 mg of DNA. "Total DNA" and "total nucleic acid" refers to a pool of nucleic acids encoding distinct antigens. For example, a dose of 5 mg of total DNA encoding 5 different poxvirus antigens can have 1 mg of each antigen. DNA vaccines can be administered multiple times, e.g., between two-six times, e.g., three times. In an exemplary method, 100 μg of a DNA composition is administered to a human subject at 0, 4, and 12 weeks (100 μg per administration).

Protein Compositions

Proteins, e.g., recombinant proteins, which are antigens of poxviruses, can be administered as vaccines or as vaccine "boosts" following vaccination with nucleic acid compositions. Recombinant proteins can also be administered in conjunction with other immunogenic compositions (e.g., live attenuated vaccinia vaccine preparations). Recombinant proteins (e.g., proteins produced by cloning DNA encoding antigens of poxvirus isolates using standard molecular biological techniques) can be one source of isolated proteins for boosting. Proteins used for boosting an individual can include the same sequences as encoded by the DNA vaccines previously administered to the individual, e.g., vaccinia D8L, A27, B5, L1R, or A33R, or portions thereof.

For large-scale production of recombinant viral proteins, transfectant cell lines are generated (e.g., Chinese Hamster Ovary cell transfectants), and cell lines that stably express the proteins are generated from the transfectants. Lines that overexpress the protein are selected for production. Master and working cell banks of selected cells are maintained. Proteins are expressed by growing cells in large-scale cultures in protein-free medium. Supernatants of the cells are harvested. Protein is then purified (e.g., using affinity chromatography, ion exchange chromatography, and/or gel filtration chromatography), and tested for purity. Proteins are purified and concentrated using techniques such as gel filtration and ion exchange chromatography. Next, proteins are evaluated for identity, potency, purity, quantity, sterility, the presence of endotoxin, and general safety according to Good Manufacturing Practice (GMP) guidelines. Identity can also be determined with ELISA with antibodies specific for the clade of the protein. Potency can also be evaluated with ELISA (e.g., reactivity of rabbit sera with the purified protein). Purity can be evaluated With SDS-PAGE and silver stain analyses of the protein, and size-exclusion high-performance liquid chromatography. Quantities can be determined by Coomassie-based assays, spectrophotometric assays, and volume measurements. The quality of protein preparations can be determined by visual inspection and pH measurements. Sterility can be determined by methods described in 21 C.F.R. 610.12. Endotoxin can be determined by Limulus Amebocyte assays. General safety can be determined by methods described in 21 C.F.R. 610.11.

Protein compositions containing an immunogenically effective amount of a recombinant poxvirus protein, or fragments thereof, can be administered by various routes and methods of administration. Suitable compositions can include, for example, lipopeptides (e.g., Vitiello et al., 1995, J. Clin. Invest., 95:341), peptide compositions encapsulated in poly(DL-lactide-co-glycolide) ("PLG") microspheres (see, e.g., Eldridge et al., 1991, Molec. Immunol., 28:287-94; Alonso et al., 1994, Vaccine, 12:299-306; Jones et al., 1995, Vaccine, 13:675-81), and peptide compositions contained in immune stimulating complexes (ISCOMS) (see, e.g., Takahashi et al., 1990, Nature, 344:873-75; Hu et at, 1998, Clin. Exp, Immunol., 113:235-43).

Useful carriers that can be used with the immunogenic compositions and vaccines described herein are well known, and include, for example, thyroglobulin, albumins such as human serum albumin, tetanus toxoid, polyamino acids such as poly L-lysine and poly L-glutamic acid, influenza, hepatitis B virus core protein, and the like. The compositions and vaccines can contain a physiologically tolerable (i.e., acceptable) diluent such as water, or saline, typically phosphate buffered saline. The compositions and vaccines also typically include an adjuvant. Adjuvants such as QS-21, incomplete Freund's adjuvant, aluminum phosphate, aluminum hydroxide, or alum, are examples of materials well known in the art. Additionally, CTL responses can be primed by conjugating S proteins (or fragments, derivative or analogs thereof) to lipids, such as tripalmitoyl-S-glcerylcysteinyl-seryl-serine ($P_3CSS$).

Immunization with a composition containing a poxvirus protein composition, e.g., via injection, aerosol, oral, transdermal, transmucosal, intrapleural, intrathecal, or other suitable routes, induces the immune system of the host to respond to the composition.

An exemplary range for an immunogenic amount of protein composition is 5 µg/kg-500 µg/kg, e.g., 10-100 µg/kg of total protein, with adjuvant. In one embodiment, a dose of 325 µg of a protein composition is administered to a human (18-55 years of age, 45-75 kg). An exemplary program of administration of the protein composition includes a first intramuscular boost 8 weeks after the final nucleic acid immunization, followed by a second intramuscular boost with the protein composition 8 weeks after the first boost.

The immunogenic DNA and protein compositions described herein can be administered to subjects at risk for exposure to variola, and to laboratory workers who are exposed to vaccinia, cowpox, monkey pox, variola, or other members of the *Orthopoxvirus* genus.

Kits

Kits comprising the nucleic acid and protein compositions are provided. The kits can include one or more other elements including: instructions for use; other reagents, e.g., a diluent, devices or other materials for preparing the composition for administration; pharmaceutically acceptable carriers; and devices or other materials for administration to a subject. Instructions for use can include instructions for therapeutic application (e.g., DNA vaccination and protein boosting) including suggested dosages and/or modes of administration, e.g., in a human subject, as described herein.

The kit can further contain at least one additional reagent, such as a diagnostic or therapeutic agent, e.g., a diagnostic agent to monitor a response to immune response to the compositions in the subject, or an additional therapeutic agent as described herein.

In one embodiment, the kit includes a vial (or other suitable container) containing nucleic acids encoding two, three, four, five, or six distinct poxvirus antigens. The kit also includes a second vial containing recombinant poxvirus polypeptides (e.g., polypeptides that are the same as those encoded by the nucleic acids in the kit). The kit can include QS-21 adjuvant (50 µg/dose/subject) and cyclodextrin as an excipient (30 mg/subject). The adjuvant and the excipient are formulated with the protein, and can be included in the formulation or packaged separately within the kit.

Evaluating Immune Responses to Vaccinations

ELISA assays and Western blots can be used to assess humoral immune Responses. In particular, ELISA and Western blots can be used to assess antibody binding, antibody neutralizing capability, antibody-mediated fusion inhibition, and antibody-dependent cytotoxicity.

Techniques for evaluating cellular immune responses include intracellular staining (e.g., flow cytometry) and ELISPOT (an enzyme-linked immunosorbent assay format), which allow detection and quantitation of cells producing cytokines (e.g., TNFα and IFN-γ) in response to antigens. For example, isolation of splenocytes or peripheral blood monocyte cells (PBMCs) from animals or human patients followed by in vitro challenge with a poxvirus antigen such as D8, and finally testing by ELISPOT and/or intracellular cytokine staining (ICS), can determine the potential for a cell-mediated immune response in vaccine recipients. A standard chromium release assay can be used to assess cytotoxicity. To assess a cell-mediated immune response to a DNA vaccine, the traditional approaches of measuring T cell proliferation in response to antigen and CTL-mediated killing of autologous cells expressing poxvirus epitopes can also be used.

EXAMPLES

The invention is further described in the following examples, which do not limit the scope of the invention described in the claims.

Example 1

Construction and Expression of DNA Vaccines Expressing Vaccinia D8 Antigens

The gene encoding the D8 protein was cloned into a DNA vaccine vector pSW3891, which uses a CMV IE promoter, and an Intron A sequence downstream of the CMV promoter, to drive the expression of coded antigen insert (Wang et al., 2005, J. Virol., 79(3):1906-1910). To produce more immunogenic D8L DNA vaccines, two versions of D8L gene inserts were produced (FIG. 1). The first one, wtD8L, has a full length coding sequence of the wild type D8L gene. The second one, tPAD8L, encodes a D8protein with an N-terminal human tissue plasminogen activator (tPA) leader sequence and a deletion of the transmembrane (TM) region and cytoplasmic tail. The wild type D8L gene does not encode a natural leader sequence.

To construct the wtD8L DNA vaccine, the D8L gene was PCR amplified from WR strain of vaccinia virus (VACV) using pfu DNA polymerase (Stratagene, Calif.). DNA inserts were then subcloned into pSW3891 after the CMV immediately early (IE) promoter (Wang et al., 2005,J. Virol., 79(3): 1906-1910). For the tPA-D8L construct, the PCR amplified genes were subcloned into the same vector downstream of the tPA leader sequence (Lu et al., 1998, Meth. Molec. Med., 29:355-374; Wang et al., 2004, Vaccine 22(25-26):3348-3357; Wang et al., 2006, Vaccine, 24(21):4531-4540). Each DNA vaccine plasmid transformed in E. coli (HB101 strain) was checked by restriction digestion and DNA sequencing before large amounts of DNA plasmids were prepared with a Mega purification kit (Qiagen, Valencia, Calif.).

Additional vaccinia genes (A27L, B5R, L1R, and A33R) were PCR amplified from WR strain of VACV using pfu DNA polymerase subcloned into pSW3891 after the CMV immediately early (IE) promoter (Wang et al., 2005, J. Virol., 79(3):1906-1910). Studies with these constructs are described below.

Expression of D8 from the DNA vaccines was examined by Western blot using culture supernatants and cell lysates from 293T cells transiently transfected with each of these two D8L DNA vaccine plasmids. Cells were transiently transfected by a calcium phosphate co-precipitation method using 10 μg of plasmid DNA for $2 \times 10^6$ cells in a 60-mm dish. Cells were harvested 72 hours later. Both supernatants and cell lysates were collected for ELISA or Western blot analysis.

To produce the D8-specific rabbit sera used for the Western blot analysis of D8 antigen expression described above, New Zealand White (NZW) rabbits of 2-3 kg body weight were purchased from Millbrook Farm (Amherst, Mass.). Each rabbit received 3 bi-weekly immunizations of 36 μg D8L DNA vaccines at each immunization by a gene gun at the shaved abdominal skin. Sera were collected 2 weeks after the last immunization. D8-specific rabbit serum R274 was used for Western blot analysis.

To perform Western blots, 10 ng of protein/sample was resolved by SDS-PAGE and transferred onto PVDF membranes (Bio-Rad, Hercules, Calif.). Membranes were blocked overnight at 4° C. in blocking buffer (0.2% IQblock, 0.1% Tween®-20 in 1X PBS). Membranes were incubated with a 1:300 dilution of antisera from a rabbit immunized with D8L. After washing, blots were incubated with alkaline phosphatase-conjugated goat anti-rabbit IgG (Tropix, Bedford, Mass.) at 1:5000 dilution for 1 hour at room temperature, and signals were detected using a chemiluminescence Western-Light Kit (Tropix, Bedford, Mass.).

The tPA D8L DNA vaccine was expressed at a higher level than the wtD8L construct. The tPA-D8L was particularly effective at increasing the secretion of D8 antigen to supernatants. When analyzed by SDS-PAGE, the apparent molecular weight of tPA-D8L protein was higher than wtD8L in supernatant, suggesting additional post-translational processing steps for this modified D8L gene design. One possibility was the glycosylation of D8 protein since tPA-D8L has three putative N-glycan sites (N29, N94 and N144). To examine this, transiently expressed tPAD8L proteins were treated with peptide N-glycosidase F (PNGaseF). PNGaseF (New England Bio Lab, Beverly, Mass.) was added to denatured samples prepared from the supernatants of transiently transfected 293T cells according to manufacturer's instructions. After incubating overnight at 37° C., samples were resolved by SDS-PAGE and analyzed by Western blot as described above.

PNGaseF reduced the molecular weight of D8 both in lysate and supernatant to that of the precursor form of D8, indicating that newly expressed tPA-D8L in 293T cells was glycosylated. Interestingly, D8 expressed by vaccinia virus was primarily non-glycosylated, based on its apparent molecular weight and resistance to PNGaseF treatment. The identity of newly expressed D8 antigen was further confirmed by the strong reactivity between mouse sera immunized with vaccinia virus and the tPA-D8L protein expressed in 293T cells.

Example 2

Immunogenicity of the D8L DNA Vaccines

The immunogenicity of both forms of D8L DNA vaccines was tested in BALB/c mice. Control groups of mice received either empty vector DNA (negative control) or were administered vaccinia virus WR strain (positive control).

Six to eight week old female BALB/c mice were purchased from Taconic Farms (Germantown, N.Y.). The animals were immunized with a Helios® gene gun (Bio-Rad Laboratories, Hercules, Calif.) at the shaved abdominal skin as previously reported (Wang et al. 2004, Methods Mol. Biol., 245:185-196).

Each mouse received 4 bi-weekly immunizations with six DNA shots of 2 μg each per immunization. Mice immunized with VACV received $10^5$ pfu of VACV in 10 μl PBS by intradermal inoculation into the ear pinnae 1 month before challenge (Tscharke et al., 2002,J. Gen. Virol., 83:1977-1986; Tscharke and Smith., 1999, J. Gen. Virol., 80:2751-2755). At least 5 mice were included in each group for immunogenicity studies. Blood samples were collected periorbitally prior to the first immunization and 2 weeks after each immunization.

To measure antibody responses by ELISA, individual mouse sera from each animal group were collected. ELISA plates were coated with 100 μl of antigen at 1 μg/ml harvested from 293T cells transiently transfected with the DNA vaccine plasmids and incubated overnight at 4° C. In addition to measuring reactivity to recombinant D8L antigen produced in transfected 293T cells, antisera were tested for reactivity to lysates of Vero cells infected with vaccinia virus WR strain. For the latter assays, ELISA plates were coated with $10^5$ pfu of vaccinia virus (VACV) per well and fixed with 2% paraformaldehyde (Wyatt et al., 2004, Proc. Natl. Acad. Sci. U.S.A. 101(13):4590-4595). The WR strain of VACV used in these studies was propagated in Vero cells. Clarified cell lysates were used for Western blot analysis and ELISA. VACV stock for challenge was prepared in L929 cells (Selin et al., 1994, J. Exp. Med., 179(6):1933-1943) and purified from serum contaminants by centrifugation on sucrose gradients (Chen et al., 2001, Nat, Immunol., 2(11):1067-1076). Viral titer assays were performed on Vero cells (Selin et al., 1994, J. Exp. Med., 179(6):1933-1943; Selin et al., 1998, J. Exp. Med., 188(9):1705-1715).

Serially diluted mouse sera (100 μl) were added to each well and assayed in duplicate after blocking. The plates were incubated with biotinylated anti-mouse IgC (Vector Laboratories, Burlingame, Calif.) diluted at 1:1000 (100 μl per well), followed by horseradish peroxidase-conjugated streptavidin (Vector Laboratories) diluted at 1:2000 and finally developed with 3,3-,5,5-tetramethybenzidine (Sigma-Aldrich, St. Louis, Mo.) solution (100 μl per well). The reactions were stopped by adding 25 μl of 2M $H_2SO_4$, and the plates were read at OD450 nm. The endpoint titer was calculated as the serum dilution resulting in absorbance greater than 2 standard deviations above the absorbance in wells incubated with negative control mouse serum.

Serum anti-D8 IgG responses increased with each immunization as measured by ELISA (data not shown) and they reached the peak level at 2 weeks after the fourth DNA immunization (FIGS. 2A-2C). Both wtD8L and tPA-D8L DNA vaccines elicited positive anti-D8 IgG responses. The geometric mean titer of the tPA-D8L, DNA vaccine group was higher than the wtD8L DNA vaccine group, as measured against both the recombinant D8 antigen produced from 293T cells (FIG. 2A) or the lysates of Vero cells infected with the vaccinia virus (FIG. 2B).

As expected, the positive control mouse sera, from animals immunized with the vaccinia virus WR strain, had higher titers against the cell lysates infected with the vaccinia virus than the recombinant D8 antigen due to the presence of multiple poxvirus antigens in the infected cell lysates. Likewise, the levels of D8-specific antibodies elicited by both D8L DNA vaccines were higher than that elicited by the vaccinia virus WR strain, presumably due to the fact that anti-D8 antibody is only part of the broad antibody responses against a wide range of antigens in sera immunized with vaccinia viruses.

To measure neutralizing antibody responses elicited by the DNA vaccines, plaque neutralizing assays were performed. Fifty percent plaque reduction titer was determined by standard techniques (Frey et at., 2002, N. Engl. J. Med., 346(17): 1275-1280). Briefly, sera from immunized animals were heat inactivated for 30 minutes at 56° C. and serial dilutions of antibodies were incubated with 50 pfu of VACV for 1 hour at 37° C.

Confluent Vero cells monolayers were infected with antibody-virus mixtures for 1 hour, washed with PBS and incubated under liquid overlay for 2 days. Monolayers were then stained with 0.5% of crystal violet for 5 minutes and plaques were counted. The neutralization was calculated as the percentage of the number of plaque counts reduced at the testing serum in an assay compared to the mean of the plaque counts for the three virus controls (without sera) in the same assay.

The mouse sera elicited by D8L DNA vaccines were able to neutralize vaccinia virus as measured in a plaque reduction assay (FIG. 2C). The tPA-D8L DNA vaccine induced higher neutralizing antibodies than the wtD8L DNA vaccine. It was unexpected. that the neutralizing titer of anti-tPA-D8L sera was almost the same as that of the mouse sera immunized with the vaccinia virus (FIG. 2C). It appears that either high titers of antibodies against one major poxvirus antigen (such as D8) or relatively lower titers of immune sera against multiple poxvirus antigens could achieve the same neutralizing effect as measured by this in vitro neutralization assay against the IMV form of poxvirus.

Example 3

Protective Efficacy of D8L DNA Vaccines in Mice Against Lethal Vaccinia Challenges The protective potential of D8 antigen, either alone or in combination with other reported protective poxvirus antigens, was evaluated in BALB/c mice against lethal vaccinia challenge. In this series of challenge studies, each mouse received four bi-weekly gene gun-mediated DNA vaccinations with a fixed total dose of 12 μg DNA plasmids at each vaccination.

First, protection studies against a lethal dose of vaccinia virus ($5\times10^7$ pfu per animal) delivered by intraperitoneal (i.p.) route were conducted. Age matched female BALB/c mice (10 per group) were used in all experiments. Two weeks after the last immunization, BALB/c mice were anesthetized intramuscularly with ketamine-xylasine and then injected with $5\times10^7$ pfu WR strain of VACV in 100 μl of PBS by intraperitoneal route. Alternatively, BALB/c mice at 2 weeks after the last immunization received $5\times10^6$ pfu WR strain of VACV in 25 μl of PBS by intranasal inoculation. Mice were weighed and observed daily as previously described (Selin et al., 1994, J. Exp. Med. 179(6):1933-1943).

As a result of the high dose virus challenge, control mice inoculated with empty DNA vector lost weight progressively until death as early as 3-4 days after challenge (FIG. 3A; Table 2, below). Both forms of D8L DNA vaccines, when delivered alone, were able to protect mice from continuous weight loss and ultimate death as compared to the control group mice that received the empty DNA vector (FIG. 3A). None of the D8L DNA vaccinated mice died. The tPA-D8L DNA vaccine appears slightly more effective in controlling the weight loss than the wtD8L DNA vaccine, but neither of them were quite as effective as the positive control immunization with vaccinia virus WR strain in controlling weight loss (FIG. 3A). This result is consistent with the previous reports that a single poxvirus antigen vaccine could not achieve the same level of protection provided by the live attenuated poxvirus vaccines (Fogg et al., 2004, J. Virol. 78(19):10230-10237; Hooper et al., 2000, Virology 266(2): 329-339; Pulford et al., 2004, Vaccine 22(25-26):3358-3366). However, these data are the first report that D8 antigen alone was able to achieve a 100% protection from death by a lethal vaccinia challenge.

TABLE 2

Average weight loss after VACV challenge

| | A27L/B5R | | D8L/A27L/B5R | | P value (paired |
|---|---|---|---|---|---|
| Day | % of initial weight | Standard deviation | % of initial Weight | Standard deviation | Student's t test) |
| 0 | 100 | 0 | 100 | 0 | N/A |
| 1 | 90.6 | 2.5 | 93.6 | 1.5 | $p > 0.05$ |
| 2 | 89.5 | 3.5 | 95.2 | 1.8 | $p < 0.05$ |
| 3 | 90.8 | 3.8 | 97.7 | 1.7 | $p < 0.05$ |
| 4 | 93.4 | 5.8 | 99.7 | 0.8 | $p > 0.05$ |
| 5 | 94.6 | 8.9 | 99.2 | 0.9 | $p > 0.05$ |

Next, we evaluated the D8L DNA vaccine in combination with other subunit-based polyvalent poxvirus vaccines to determine whether the addition or D8L improved the efficacy of the polyvalent vaccines. A DNA vaccine construct with the tPA-D8L insert was used in this study, because measurements on both antibody response and weight loss indicated that the tPA-D8L DNA vaccine was more effective than the wtD8L DNA vaccine. DNA vaccines were subcloned into the pSW3981 vector.

DNA vaccines were administered i.p., and animals were challenged with VACV, as described above. The efficacy of a bivalent formulation with two poxvirus antigens, A27 and B5, was significantly improved with the addition of tPA-D8L DNA vaccine as the third component (FIG. 3B). Mice immunized with bivalent formulation had lost 9.2% of weight on day 3 after challenge, whereas mice immunized with the 3-valent formulation including A27, B5, and D8 had lost only 2.3% ($p<0.05$). Protection provided by this 3-valent formulation was similar to that provided with the vaccinia virus vaccination. Addition of a D8 antigen also improved the protective efficacy of a 4-valent formulation (A27, B5, L1, and A33) by minimizing the weight loss during the first 1-3 days after challenge (FIG. 3C) when studied in the same i.p.

challenge model. Mice immunized with the 5-valent formulation that included D8 antigen regained initial body weight at 2.5 days after challenge, as compared to 4.2 days in the 4-valent formulation group that did not include D8 (p<0.05).

Figure 4B:
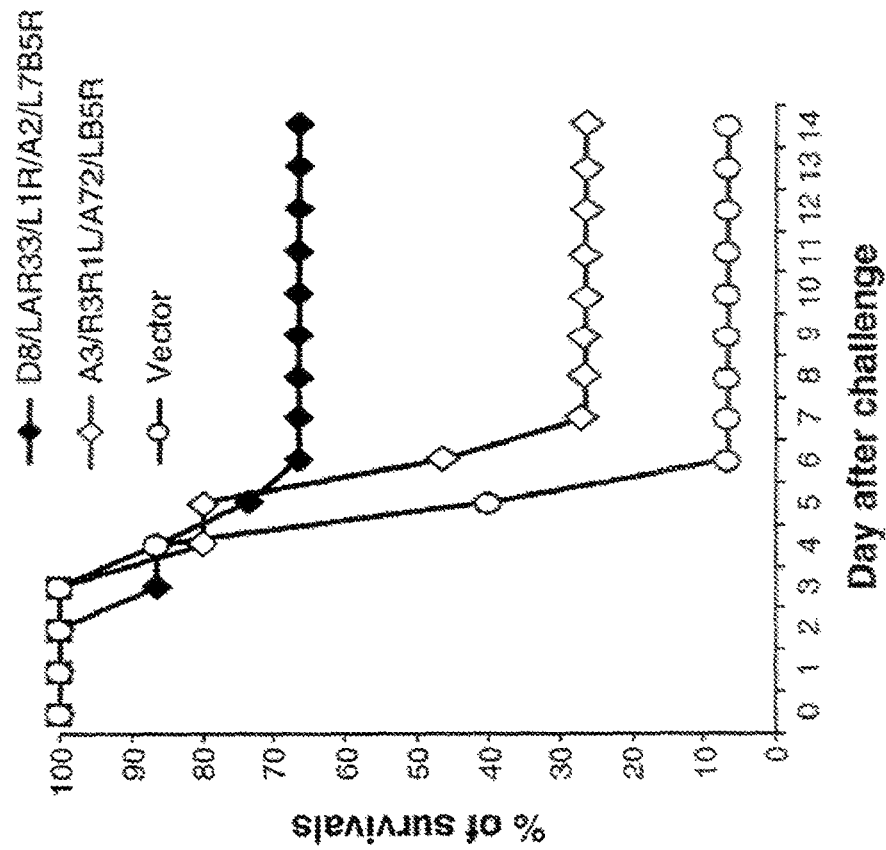
FIG. 4B is a graph depicting percent survival at each day post-challenge. Curves represent data from the same mice as depicted in FIG. 4A.
Figure 4A:
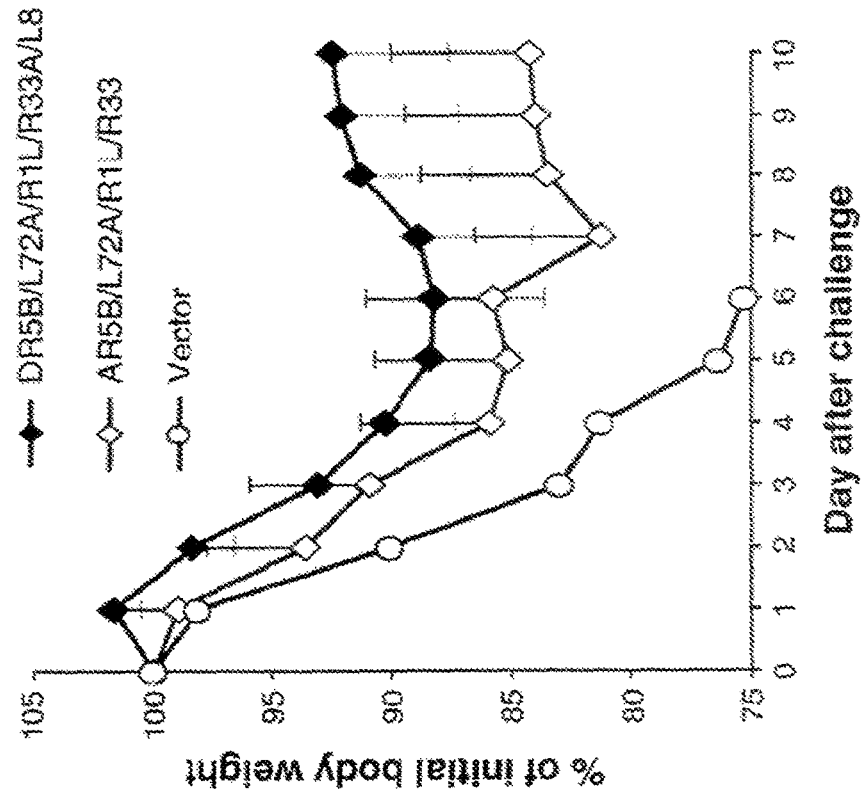
FIG. 4A is a graph depicting body weight loss as the percentage of pre-challenge weight in mice challenged with vaccinia virus WR strain by the intranasal route 2 weeks after the last DNA immunization. Mice were immunized with a 4-valent pox DNA formulation (A27L, B5R, L1R, and A33R) with or without the addition of a fifth component (tPA-D8L). Each curve shows the group average weight loss of surviving mice (15 per group initially).

The above finding was further confirmed in an airway infection model in which mice were challenged with $5 \times 10^6$ pfu of vaccinia virus delivered by the intranasal (i.n.) route as previously reported (Galmiche et al., 1999, Virology, 254(1): 71-80). In this study, mice that received the 5-valent formulation including D8 not only had stopped losing weight earlier than those that received the 4-valent formulation (FIG. 4A), but also achieved 66% protection (10 out of 15 mice) as compared to the 26% protection (4 out of 15) by the 4-valent formulation against lethal challenge (FIG. 4). The difference in survival between two formulations was statistically significant (p<0.05), but the difference in body weight loss was not.

Statistical analyses described herein were performed using Epi Info™ software for windows available from the CDC web site. Survival curves were analyzed using Kaplan-Meier test. Comparisons between the mean percentage body-weight changes for different groups at each day after challenge were performed using an unpaired, two-tailed Student's t test (Microsoft Excel software, version 2003) in consultation with a biostatistician. Significance levels were set at a P value less than 0.05.

Example 4

Antibody Responses Induced by Polyvalent Vaccine Formulations in Mice

To further characterize the specific antibody responses against individual pox antigens included in the polyvalent vaccine formulation and vaccinia vaccine, more detailed analyses were conducted with mice sera immunized with different polyvalent vaccine formulations included in the above animal studies.

A27, D8, and L1 are highly immunogenic antigens. Anti-A27 antibody had the highest titers especially when Mice received the bivalent (A27 and B5) formulation (FIG. 5A). Anti-D8 antibody titers remained high in mice immunized with either 3-valent or 5-valent formulations (FIG. 5C). Similarly, anti-L1 antibody titers were high in mice immunized with either 4-valent or 5-valent formulations (FIG. 5D). B5 was less immunogenic with lower antibody titers against the autologous antigen (FIG. 5B) A33 was the least immunogenic among antigens included in the 4-valent and 5-valent formulations (FIG. 5E). It should be noted that since ELISA assays were carried out with crude lysates of cells transiently transfected with the DNA vaccines, low titers of anti-A33 antibodies may be attributed to either a low level of specific IgG or to a low level of A33 expression in 293T cells. However, induction of anti-vaccinia antibodies by A33 DNA immunization was indeed confirmed by Western blot against vaccinia virus (data not shown).

In our study, the total DNA vaccine dose was fixed no matter how many antigen components were included in various polyvalent formulations. There was a decrease of less than 10-fold in anti-A27 titers when D8 was added to the bivalent formulation containing A27 and B5. Otherwise, the levels of antigen specific antibody responses showed only a small decrease when more poxvirus antigens were added, suggesting that the effect of antigen dilution due to the addition of new antigens was present, but not significant. Mouse sera immunized with the vaccinia vaccine had positive antibodies against each of the five poxvirus antigens, confirming that these proteins were effective antigens during vaccinia immunization. However, the levels of such antibodies varied. Anti-D8 IgG titer was the highest and anti-A33 IgG titer was the lowest. Both vector control sera and sera lacking a particular antigen did not show specific reactivity against that antigen.

Sera from mice immunized with polyvalent DNA vaccines had high titers of IgG responses against VACV antigens, and such titers increased when more antigens were added to the polyvalent DNA vaccine formulations (FIG. 5F). On the other hand, the anti-VACV titer for vaccinia virus immunized mouse sera was lower than most of the polyvalent formulations. This finding suggested that while the vaccinia virus could induce antibody responses against a very broad array of poxvirus antigens, subunit-based polyvalent formulations could develop higher total antibody responses even with fewer antigens. More importantly, titer of anti-VACV antibody response (FIG. 5F) did not correlate with protection (FIGS. 3A-5G).

Levels of neutralizing antibody responses were also analyzed. In our assay, the neutralizing antibodies mainly targeted the IMV form of the poxvirus. Each of the polyvalent formulations included elicited positive neutralizing antibody responses at levels similar to or even better than that induced by the vaccinia vaccine (FIG. 5G). The 3-valent formulation including D8L elicited the strongest neutralizing antibody responses, presumably due to the combination of two strong IMV antigens, A27 and D8. The 5-valent formulation was somewhat less effective in generating neutralizing antibodies, most likely due to the diluting effect when the numbers of antigen components were increased. Interestingly, protection was not correlated with the levels of IMV-mediated neutralizing antibody responses. Rather, better protection was achieved with more antigens included in the vaccine formulations.

Example 5

Sequence Homology Between Variola Major and Vaccinia Protective Antigens

Although poxviruses are highly conserved in the regions that encode protective antigens, it is possible that antibodies induced by variola antigens may confer a higher level of protection against smallpox challenge as compared to those responses induced by vaccinia antigens. A protein subunit-based vaccine or DNA plasmid vaccine does not incorporate live viruses into its design and therefore eliminates the safety concerns over using a live smallpox virus vaccine as a means to induce responses to variola antigens.

As a first step in the production of variola sequence-based vaccines, amino acid sequences of three well-characterized protective antigens (A27, B5, and D8) from VACV were compared with orthologous proteins from the variola major (VARV) virus (FIG. 6). Sequences of *orthopoxviruses* were derived from the NCBI genome database and aligned using MacVector 7.0. For VACV sequences, two frequently used strains, Western Reserve (WR) and Copenhagen (COP), were included for the analysis. For VARV, the India 1967 (VARV-IND) and Bangladesh 1975 (VARV-BSH) strain sequences were used. The orthologous VARV protein for the VACV A27 antigen is A30 for VARV-IND and A31 for VARV-BSH; for the B5 antigen the orthologous protein is B7 for VARV-IND and B6 for VARV-BSH, and for the D8 antigen the orthologous protein for both VARV-IND and VARV-BSH is F8 (Shchelkunov, 1995, Virus Genes, 10(1):53-71; Shchelkunov et al., 1995, Virus Res., 36(1):107-18).

Sequences of these three proteins are highly homologous, but not completely identical to the VACV antigen sequences: three amino acid differences exist between A27 and A30/A31, 23 amino acid differences between B5 and B6/B7, and 12 amino acid differences between D8 and F8 proteins (FIG. 6, which shows the portions of sequences that include amino acid differences, in bold font). Some of these differences occurred in only one of the two VARV strains. Employing variola sequences can minimize the chance of reduced protection due to these sequence differences that exist between the variola and vaccinia antigens, particularly when antigen-specific immune responses, such as neutralizing antibody determinants and/or dominant T-cell epitopes, are involved.

Example 6

Construction of Codon Optimized VARV DNA Vaccines and Production of Recombinant A30, F8, and B7 in an *E. coli* Expression System Codon modified A30L, B7R, and F8L genes of Variola Major India1967 (VARV-IND) sequences were chemically synthesized. Variola sequences were altered to include codons used by mammalian cells and *E. coil* cells without changing the amino acids encoded by the sequences. To achieve this effect, codons that are most preferred for expression (i.e., most efficiently translated) in both human cells and in *E. coil* cells were substituted for certain viral codons. However, some codons that are most preferred for mammalian expression are not most preferred for bacterial expression. For these codons, both mammalian and *E. coli* preferred codons and codon with intermediate efficiency in both types of cells may be used to substitute the viral codon. For example, the mammalian cell most preferred codon is "GCC" for the amino acid Alanine "Ala" while the most preferred codon is "GCT" in *E. coli*, therefore, "GCT" or "GCC", or an intermediate codon, "GCA", may be used in the codon optimized sequence. In addition, during the sequence optimization, the following cis-acting sequence motifs are avoided: internal TATA-boxes, chi-sites and ribosomal entry sites; AT-rich or GC-rich sequence stretches; ARE, INS, CRS sequence elements; cryptic splice donor and acceptor sites; and branch points.

Codon optimization of DNA vaccines improves antigen expression and immunogenicity in mammals and permits high levels of expression in bacteria. The codon optimized synthetic genes encoding VARV A30, F8, or B7 proteins were individually cloned into the DNA vaccine vector pSW3891 immediately after the CMV immediate early (IE) promoter (Wang et al., 2005, J. Viral., 79(3):1906-10). Tables 3-5 provide a comparison of codon usage in the wild type A30L, B7R, and F8L gene sequences and the codon optimized gene sequences that were produced.

TABLE 3

Comparison of codon usage between wild type and codon optimized A30L gene sequences

| Codon | Amino Acid | Wild type gene | Codon optimized gene |
|---|---|---|---|
| GCG | Ala | 9 | 0 |
| GCA | | 27 | 0 |
| GCT | | 55 | 27 |
| GCC | | 9 | 73 |
| AGG | Arg | 14 | 0 |
| AGA | | 14 | 14 |
| CGG | | 29 | 0 |
| CGA | | 0 | 0 |
| CGT | | 0 | 0 |
| CGC | | 43 | 86 |
| AAT | Asn | 100 | 0 |
| AAC | | 0 | 100 |
| GAT | Asp | 67 | 0 |
| GAC | | 33 | 100 |
| TGT | Cys | 100 | 0 |
| TGC | | 0 | 100 |
| TGA | End | 0 | 0 |
| TAG | | 0 | 0 |
| TAA | | 100 | 100 |
| CAG | Gln | 33 | 100 |
| CAA | | 67 | 0 |
| GAG | Glu | 27 | 100 |
| GAA | | 73 | 0 |
| GGG | Gly | 0 | 0 |
| GGA | | 75 | 0 |
| GGT | | 25 | 0 |
| GGC | | 0 | 100 |
| CAT | His | 0 | 0 |
| CAC | | 100 | 100 |
| ATA | Ile | 33 | 0 |
| ATT | | 67 | 0 |
| ATC | | 0 | 100 |
| TTG | Leu | 22 | 0 |
| TTA | | 0 | 0 |
| CTG | | 11 | 100 |
| CTA | | 33 | 0 |
| CTT | | 22 | 0 |
| CTC | | 11 | 0 |
| AAG | Lys | 38 | 100 |
| AAA | | 62 | 0 |
| ATG | Met | 100 | 100 |
| TTT | Phe | 60 | 0 |
| TTC | | 40 | 100 |
| CCG | Pro | 0 | 0 |
| CCA | | 75 | 0 |
| CCT | | 25 | 50 |
| CCC | | 0 | 50 |
| AGT | Ser | 0 | 0 |
| AGC | | 0 | 100 |
| TCG | | 0 | 0 |
| TCA | | 0 | 0 |
| TCT | | 100 | 0 |
| TCC | | 0 | 0 |
| ACG | Thr | 0 | 0 |
| ACA | | 30 | 0 |
| ACT | | 70 | 10 |
| ACC | | 0 | 90 |
| TGG | Trp | 0 | 0 |
| TAT | Tyr | 100 | 0 |
| TAC | | 0 | 100 |
| GTG | Val | 0 | 100 |
| GTA | | 25 | 0 |
| GTT | | 75 | 0 |
| GTC | | 0 | 0 |

TABLE 4

Comparison of codon usage between wild type and codon optimized B7R gene sequences

| | | % Codon usage | |
|---|---|---|---|
| Codon | Amino Acid | Wild type gene | Codon optimized gene |
| GCG | Ala | 33 | 0 |
| GCA | | 11 | 0 |
| GCT | | 44 | 67 |
| GCC | | 11 | 33 |
| AGG | Arg | 0 | 0 |
| AGA | | 0 | 0 |
| CGG | | 0 | 0 |
| CGA | | 50 | 0 |
| CGT | | 50 | 0 |
| CGC | | 0 | 100 |
| AAT | Asn | 80 | 10 |
| AAC | | 20 | 90 |
| GAT | Asp | 78 | 0 |
| GAC | | 22 | 100 |
| TGT | Cys | 95 | 0 |
| TGC | | 5 | 100 |
| TGA | End | 100 | 0 |
| TAG | | 0 | 0 |
| TAA | | 0 | 100 |
| CAG | Gln | 0 | 100 |
| CAA | | 100 | 0 |
| GAG | Glu | 15 | 100 |
| GAA | | 85 | 0 |
| GGG | Gly | 7 | 0 |
| GGA | | 47 | 0 |
| GGT | | 33 | 20 |
| GGC | | 13 | 80 |
| CAT | His | 80 | 0 |
| CAC | | 20 | 100 |
| ATA | Ile | 52 | 0 |
| ATT | | 24 | 8 |
| ATC | | 24 | 92 |
| TTG | Leu | 21 | 0 |
| TTA | | 29 | 0 |
| CTG | | 8 | 79 |
| CTA | | 25 | 0 |
| CTT | | 8 | 17 |
| CTC | | 8 | 4 |
| AAG | Lys | 5 | 86 |
| AAA | | 95 | 14 |
| ATG | Met | 100 | 100 |
| TTT | Phe | 89 | 0 |
| TTC | | 11 | 100 |
| CCG | Pro | 14 | 0 |
| CCA | | 50 | 0 |
| CCT | | 14 | 14 |
| CCC | | 21 | 86 |
| AGT | Ser | 6 | 6 |
| AGC | | 3 | 94 |
| TCG | | 16 | 0 |
| TCA | | 16 | 0 |
| TCT | | 42 | 0 |
| TCC | | 16 | 0 |
| ACG | Thr | 19 | 0 |
| ACA | | 50 | 0 |
| ACT | | 27 | 4 |
| ACC | | 4 | 96 |
| TGG | Trp | 100 | 100 |
| TAT | Tyr | 71 | 0 |
| TAC | | 29 | 100 |
| GTG | Val | 4 | 100 |
| GTA | | 27 | 0 |
| GTT | | 58 | 0 |
| GTC | | 12 | 0 |

TABLE 5

Comparison of codon usage between wild type and codon optimized F8L gene sequences

| | | % Codon usage | |
|---|---|---|---|
| Codon | Amino Acid | Wild type gene | Codon optimized gene |
| GCG | Ala | 8 | 0 |
| GCA | | 62 | 8 |
| GCT | | 15 | 15 |
| GCC | | 15 | 77 |
| AGG | Arg | 8 | 0 |
| AGA | | 42 | 0 |
| CGG | | 0 | 0 |
| CGA | | 42 | 17 |
| CGT | | 0 | 0 |
| CGC | | 8 | 83 |
| AAT | Asn | 65 | 4 |
| AAC | | 35 | 96 |
| GAT | Asp | 73 | 20 |
| GAC | | 27 | 80 |
| TGT | Cys | 100 | 0 |
| TGC | | 0 | 100 |
| TGA | End | 0 | 0 |
| TAG | | 100 | 0 |
| TAA | | 0 | 100 |
| CAG | Gln | 11 | 67 |
| CAA | | 89 | 33 |
| GAG | Glu | 53 | 93 |
| GAA | | 47 | 7 |
| GGG | Gly | 23 | 0 |
| GGA | | 69 | 15 |
| GGT | | 0 | 0 |
| GGC | | 8 | 85 |
| CAT | His | 70 | 10 |
| CAC | | 30 | 90 |
| ATA | Ile | 41 | 0 |
| ATT | | 45 | 0 |
| ATC | | 14 | 100 |
| TTG | Leu | 32 | 0 |
| TTA | | 18 | 0 |
| CTG | | 4 | 89 |
| CTA | | 25 | 4 |
| CTT | | 18 | 7 |
| CTC | | 4 | 0 |
| AAG | Lys | 22 | 100 |
| AAA | | 78 | 0 |
| ATG | Met | 100 | 100 |
| TTT | Phe | 71 | 7 |
| TTC | | 29 | 93 |
| CCG | Pro | 36 | 0 |
| CCA | | 36 | 0 |
| CCT | | 18 | 18 |
| CCC | | 9 | 82 |
| AGT | Ser | 14 | 7 |
| AGC | | 0 | 93 |
| TCG | | 14 | 0 |
| TCA | | 18 | 0 |
| TCT | | 46 | 0 |
| TCC | | 7 | 0 |
| ACG | Thr | 12 | 0 |
| ACA | | 35 | 0 |
| ACT | | 29 | 6 |
| ACC | | 24 | 94 |
| TGG | Trp | 100 | 100 |
| TAT | Tyr | 92 | 0 |
| TAC | | 8 | 100 |
| GTG | Val | 17 | 100 |
| GTA | | 67 | 0 |
| GTT | | 8 | 0 |
| GTC | | 8 | 0 |

Each DNA vaccine plasmid transformed in *E. coli* (HB101 strain) was checked by restriction digestion and DNA sequencing before large amounts of DNA plasmids were prepared with a Mega purification kit (Qiagen, Valencia, Calif.).

Expression of these codon-optimized VARV antigen DNA vaccines was verified in culture supernatants and cell lysates from 293T cells transiently transfected with each of the three VARV antigen DNA plasmids and examined by Western blot using a polyclonal anti-vaccinia virus serum. All three of these antigens were present in both the cell lysates and culture supernatant and their molecular weights matched that from the VACV-WR strain grown in Vero cells. Non-transfected 293T cells and uninfected Vero cells did not express pox-specific antigens. Recombinant A30, B7, and F8proteins (rA30, rF8, and rB7) were successfully produced and purified from an E. coil expression system using the same synthetic A30, B7, and F8 genes. These results also show that the B7 protein forms dimers in its non-denatured condition. According to sequence analysis, the B7 protein has potential sites for N-glycosylation, which was confirmed by its sensitivity to PNGase treatment (data not shown).

Example 7

Immunogenicity of the A30, F8, and B7 DNA Vaccines

Six to eight week old female BALB/c mice (Taconic Farms, Germantown, N.Y.) were immunized with a Helios® gene gun (Bio-Rad) at the shaved abdominal skin as previously reported (Wang et al,. 2004, Vaccine, 22(25-26);3348-57). Each mouse received 3-4 monthly immunizations with six DNA shots of 2 μg each per immunization. Ten mice per group were immunized. Blood samples were collected periorhitally prior to the first immunization and 2 weeks after each immunization.

Immunization with VARV DNA vaccines elicited overall high levels of antigen-specific IgG antibody responses in mice. FIGS. 7A, 7B, and 7C depict responses to A30 and A27; F8 and D8; and B7 and B5, respectively, as measured by ELISA. A30 was the most immunogenic, followed by F8and B7 DNA vaccines. As shown in the figures, antibodies induced by immunization with codon optimized variola DNA vaccines recognized both vaccinia and variola antigens expressed in the supernatant of transiently transected 293T cells. Given the polyclonal nature of the immune sera, it was not surprising that we detected no significant difference in recognition of variola or vaccinia antigens by ELISA.

Figure 8:
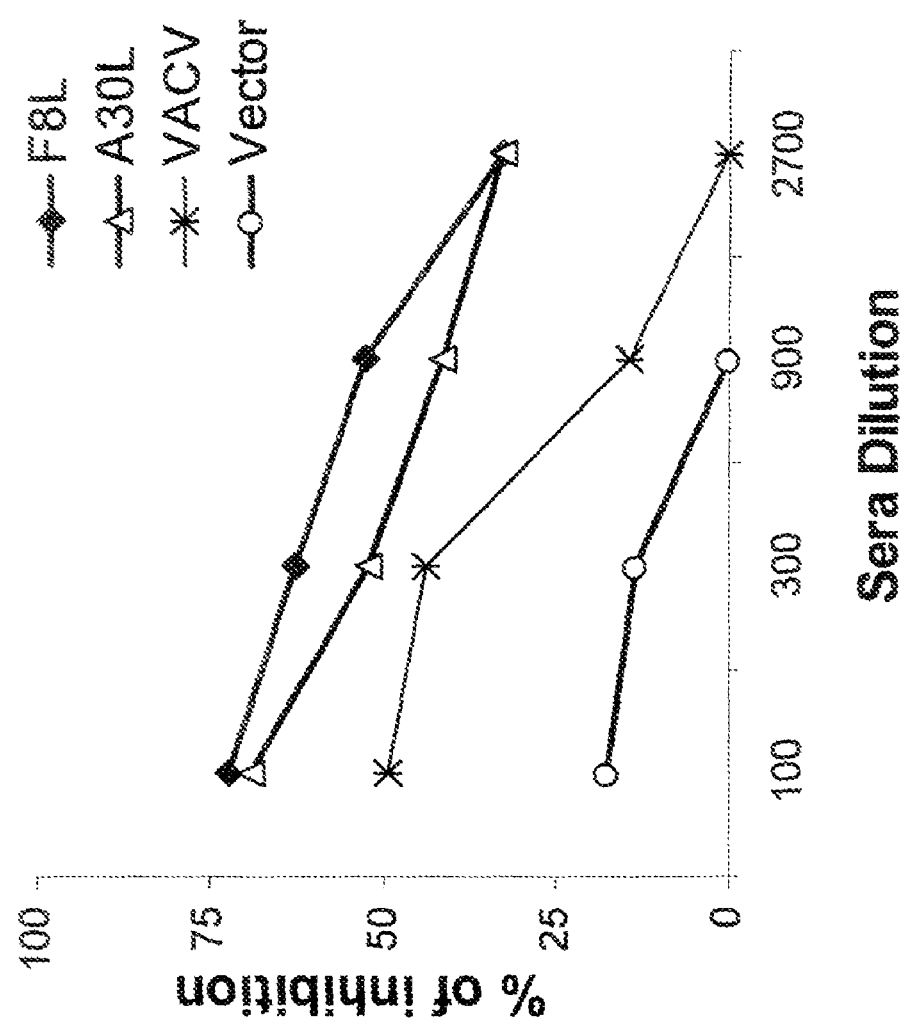
FIG. 8 is a graph depicting percent inhibition of vaccinia IMV in the presence of sera collected from Balb/C mice after three immunizations with DNA vaccines expressing either A30 or F8 antigens, as measured by a plaque reduction neutralization assay. Sera from mice immunized with vaccinia virus is shown as a positive control. Sera from mice immunized with DNA vector is shown as a negative control. Data shown are average titers from 10 mice per group.

Immunization with DNA vaccines, expressing the two VARV IMV antigens F8 and A30, produced antibodies that neutralized VACV in a plaque reduction assay that measures IMV antibodies (FIG. 8) as observed with DNA vaccines made with their VACV counterparts, D8 and A27, as described in Example 4, above. Similar to the results observed with VACV IMV antigens, the subunit VARV IMV antigens were more effective than an intact vaccinia infection in eliciting IMV neutralizing antibodies.

Example 8

Protective Efficacy of VARV DNA Vaccines Expressing A30, F8,and B7 Antigens Against Lethal VACV Challenges in Mice Protection by mono- and polyvalent DNA vaccines expressing VARV antigens was tested in a lethal VACV challenge model. Age matched female BALB/c mice (5 per group) were used in all experiments. Mice received three DNA immunizations every 2 weeks, rested 1 month, and received another boost 2 weeks prior to challenge. Mice were then inoculated intraperitoneally (i.p.) with a lethal dose ($5 \times 10^7$ pfu) of VACV (WR). Ten days after the last immunization, one group of mice was anesthetized, intramuscularly with ketamine-xylazine (100/10 mg/kg), and then injected, intraperitoneally, with $5 \times 10^7$ pfu of VACV-WR in 100 μl of PBS. Mice were weighed and observed daily, as previously described (Selin et al, 1994, J. Exp. Med., 179(6):1933-43). VARV antigen-specific antibodies after 1, 2, or 3 monovalent DNA vaccine inoculations were measured by ELISA (FIG. 9A).

Figure 9A:
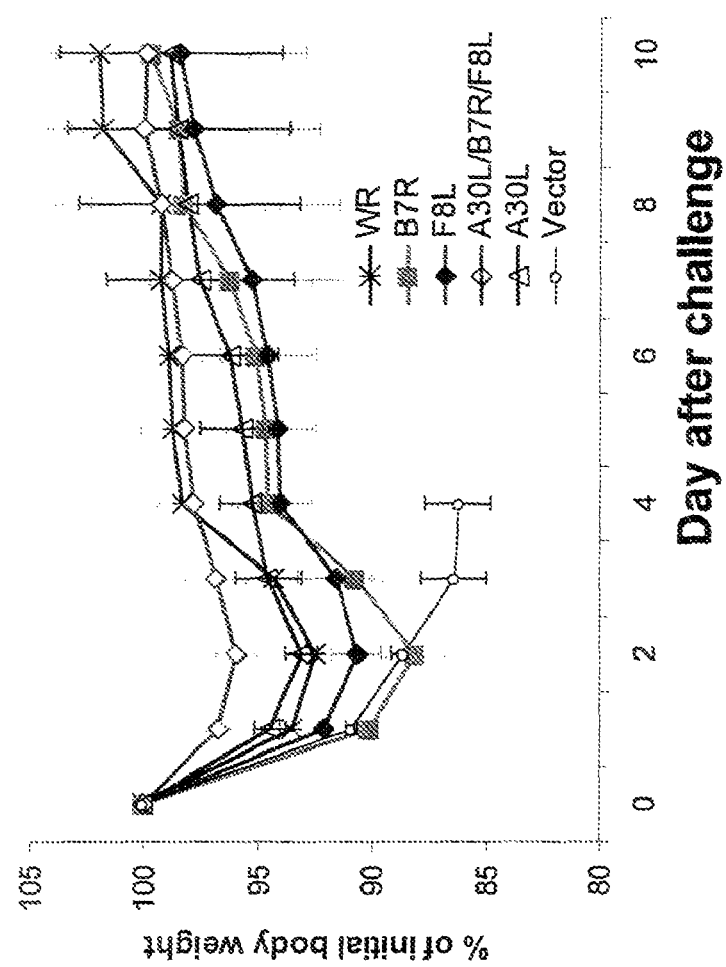
FIG. 9A is graph depicting IgG titers in sera from mice immunized with monovalent DNA vaccines expressing either A30, B7, or F8, as measured by ELISA for reactivity with the autologous antigens expressed in 293T cells. Sera were collected after one, two, or three DNA immunizations. The data are shown as the geometric mean titers of five animals.
Figure 9B:
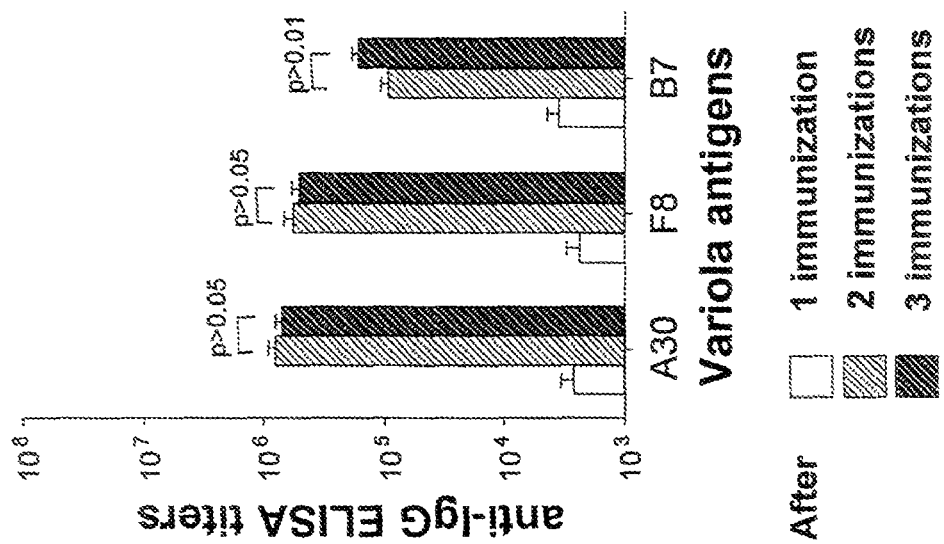
FIG. 9B is a graph depicting body weight loss shown as the percentage of pre-challenge weight in mice immunized with either monovalent vaccines or with a combination of A30L, B7R, or F8L DNA vaccines. Data for mice immunized with either the positive control vaccinia (WR) or the negative control empty DNA vaccine vector are also included. Each curve shows the group average weight loss (5 mice per group) after challenge.

FIG. 9A is a graph depicting anti-IgG ELISA titers against A30, F8, and B7 antigens in sera of immunized animals. DNA vaccines expressing each of the three VARV antigens induced high titers of antibodies to each of the A30, F8, and B7 antigens after the 2nd immunization (FIG. 9A). A third DNA vaccination was not needed to further boost the levels of antibody responses (FIG. 9A). As an indicator of protection against lethal challenge with VACV, average weight loss of the surviving mice in each group was measured. FIG. 9B is a graph depicting the percent of initial body weight following challenge. All negative control mice inoculated with the vector progressively lost weight and died by day 5. Mice that received either the mono- or polyvalent VARV DNA vaccines survived the challenge and regained body weight. Mice that received the polyvalent VARV DNA vaccine recovered their initial body weight sooner than mice that received any of the monovalent DNA vaccines (FIG. 9B).

Although intraperitoneal VACV challenge leads to lethal poxvirus infection, it does not represent the natural aerosol spread of the virus. The intranasal method of infection requires significantly less virus to produce a lethal infection and causes death at a later time point suggesting a different virus-host interaction. In addition, the intranasal mode of infection represents a more stringent challenge model. Therefore, we investigated the relative efficacy of different types of subunit-based VARV vaccines in providing protection in an intranasal challenge model.

Figures 10A, 10B:
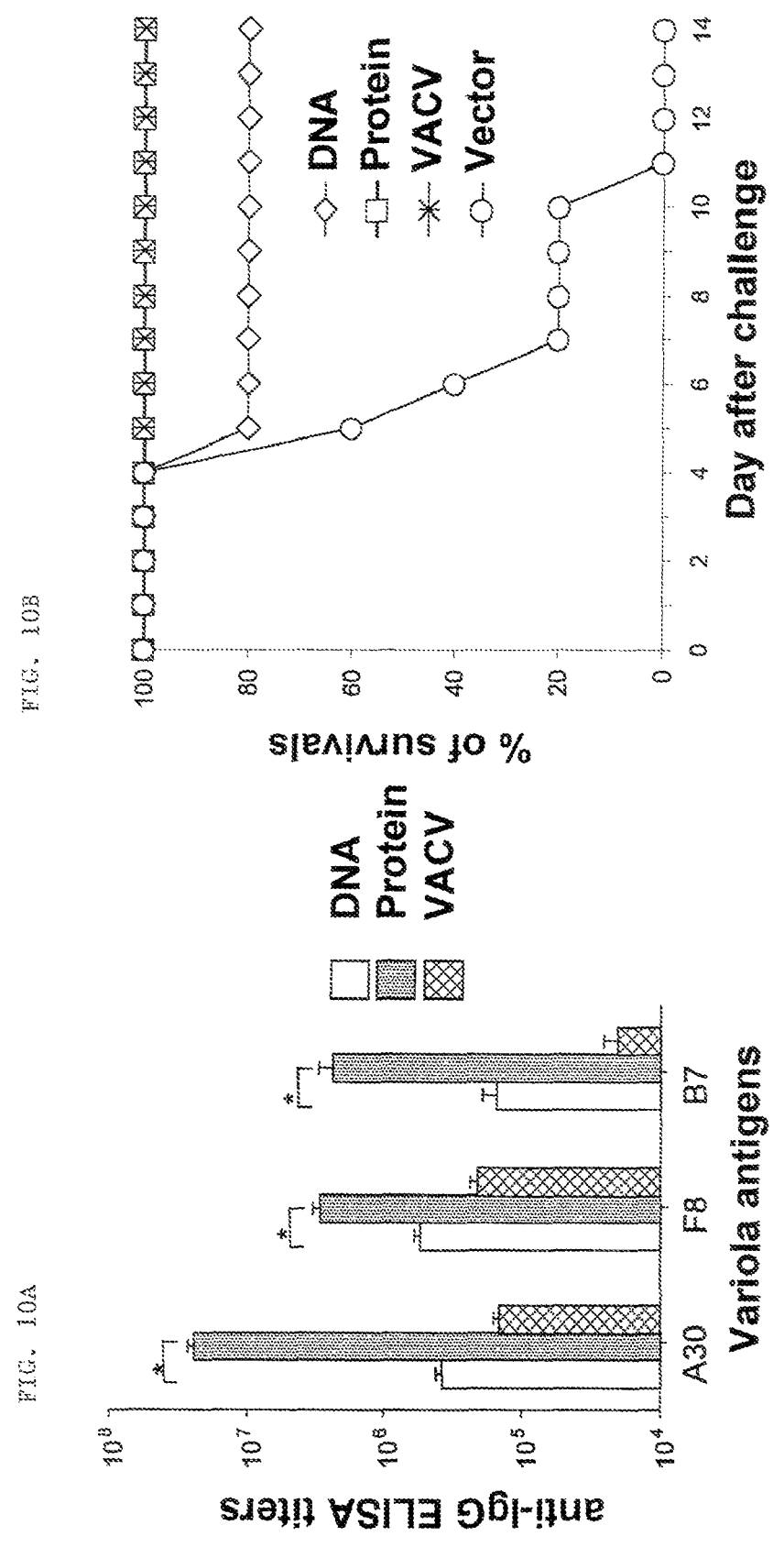

Groups of mice (five per group) were administered $5 \times 10^6$ pfu VACV-WR in 25 μl of PBS by intranasal inoculation. In this intranasal challenge study, groups of mice received 2 immunizations of either a polyvalent rA30, rB7, and rF8 protein vaccine or a polyvalent DNA vaccine expressing the A30, B7, and F8 antigens. Mice immunized with the vaccinia vaccine served as a positive control, and the negative control group received only vector DNA (FIGS. 10A-10B). Pox-specific antibodies induced by either the DNA or protein formulations and immunizations with vaccinia vaccine were analyzed by ELISA (FIG. 10A). Immunization with the polyvalent recombinant VARV protein vaccines was significantly more immunogenic than immunization with live vaccinia vaccine (p=0.0039)(FIG. 10A). In contrast, immunization with the polyvalent DNA-based VARV vaccines induced only marginally higher antibody responses when compared to immunization with VACV, except for the B7-specific antibody, which probably occurred as a result of such a low anti-B7 antibody responses in VACV immunized mice.

Mice were challenged with a lethal intranasal dose of VACV (WR) ($5 \times 10^6$ pfu) two weeks after the second immunization. While all mice in the control group died by day 11 (FIG. 10B), mice that received either the polyvalent recombinant VARV protein vaccination or the vaccinia vaccine immunization were fully protected, as indicated by a 100% survival rate following the intranasal challenge (FIG. 10B). Two immunizations with the polyvalent DNA vaccine induced partial protection with 4 out of 5 mice surviving by day 14 (80% survival, FIG. 10B). Both protein and DNA subunit vaccine formulations induced statistically significant greater levels of protection when compared to the vector control group (p=0.0017 and p=0.0211, respectively), as determined, by the Kaplan Meier survival test.

In summary, these data show that a vaccine based on antigens from the VARV virus can confer protective immunity against both intranasal and intraperitoneal challenge with the vaccinia virus and induce neutralizing antibodies against vaccinia. These studies demonstrate that a variola antigen-based vaccine is feasible and can confer increased immune responses and/or greater protection following exposure to variola.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inducing an immune response to a poxvirus in a mammal, the method comprising administering to a mammal a composition comprising at least one nucleic acid molecule comprising, a nucleotide sequence encoding a variola F8 polypeptide, wherein the nucleotide sequence is codon optimized for expression in both a mammalian cell and a bacterial cell, and has a nucleotide sequence at least 99% identical to SEQ ID NO:15, and wherein the composition is administered in an amount effective to produce an immune response in the mammal against a subsequent poxvirus infection.

2. The method of claim 1, wherein the composition further comprises a nucleotide sequence encoding one or more of variola A30 and B7 polypeptides.

3. The method of claim 1, wherein the composition comprises nucleotide sequences encoding all three of variola F8, A30, and B7 polypeptides.

4. The method of claim 2, wherein the nucleotide sequence encoding one or more of variola A30 and B7 polypeptides is codon optimized for expression in both a mammalian cell and a bacterial cell.

5. The method of claim 4, wherein the nucleotide sequence encoding the variola A30 polypeptide comprises the nucleotide sequence of SEQ ID NO:17.

6. The method of claim 4, wherein the nucleotide sequence encoding the variola B7 polypeptide comprises the nucleotide sequence of SEQ ID NO:19.

7. The method of claim 3, wherein the nucleotide sequences encoding the variola A30 and B7 polypeptides are codon optimized for expression in both a mammalian cell and a bacterial cell.

8. The method of claim 7, wherein the nucleotide sequence encoding the variola A30 polypeptide comprises the nucleotide sequence of SEQ ID NO:17.

9. The method of claim 7, wherein the nucleotide sequence encoding the variola B7 polypeptide comprises the nucleotide sequence of SEQ ID NO:19.

* * * * *

UNITED STATES PATENT AND TRADEMARK OFFICE
CERTIFICATE OF CORRECTION

PATENT NO. : 7,807,180 B2
APPLICATION NO. : 11/842761
DATED : October 5, 2010
INVENTOR(S) : Shan Lu et al.

Page 1 of 1

It is certified that error appears in the above-identified patent and that said Letters Patent is hereby corrected as shown below:

Column 1, line 6:
    delete "The work described herein was funded, in part, through a grant from the National Institutes of Health (Grant No. AI057159 awarded to Shan Lu). The United States government may, therefore, have certain rights in the invention." and replace with --The work described herein was funded through a grant from the National Institutes of Health (Grant No. AI057159 awarded to Shan Lu). Therefore, the United States government has certain rights in the invention.--

Signed and Sealed this

Thirtieth Day of November, 2010

David J. Kappos
*Director of the United States Patent and Trademark Office*